United States Patent [19]

Chou et al.

[11] Patent Number: 5,460,942
[45] Date of Patent: Oct. 24, 1995

[54] THE CATALYTIC MOIETY OF THE GLUCOSE-6-PHOSPHATASE SYSTEM: THE GENE AND PROTEIN AND RELATED MUTATIONS

[75] Inventors: Janice Y. Chou, Potomac; Ke-Jian Lei, Bethesda; Leslie L. Shelly, Rockville, all of Md.

[73] Assignee: The United States of America as represented by the Department of Health and Human Services, Washington, D.C.

[21] Appl. No.: 119,773

[22] Filed: Sep. 10, 1993

[51] Int. Cl.[6] .......................... C12N 15/11; C12N 15/55; C12Q 1/42; C12Q 1/68
[52] U.S. Cl. .......................... 435/6; 435/196; 435/320.1; 435/252.3; 435/240.1; 435/810; 536/23.2; 536/24.31; 536/24.3
[58] Field of Search .......................... 435/6, 320.1, 194, 435/196, 252.3, 240.1, 810; 536/23.2, 24.31, 24.3; 530/350

OTHER PUBLICATIONS

Kosel et al (1993) Eur. J. Pediat. 152 Suppl. 1 522–525.

Witke et al (1993) Genomics 16 751–754.

Dyer et al (1993) Biochem J. 293:51–64.

*Primary Examiner*—Robert A. Wax
*Assistant Examiner*—Rebecca Pruty
*Attorney, Agent, or Firm*—Townsend and Townsend Khourie and Crew

[57] ABSTRACT

This invention relates to nucleic acid sequences and methods useful for producing recombinant glucose-6-phosphate (G-6-Pase). In addition, the invention relates to specific mutations in the gene encoding human G-6-Pase and methods for detecting the mutations and thus diagnosing the genetic disease that causes glycogen storage disease type 1A.

19 Claims, 3 Drawing Sheets

1. THE FIVE PRIMERS USED ARE INDICATED

Fig. 2-1

```
TGCTGTCAGTCAGGTGGTCCTCTTTTACAATCCTAATCATATTGGGTAATGTTTTGAAAAAGCTAATGAAGCTATTGAGAAAGACCTGT        1609
TGCTAGAAGTTGGGTTGTTCTGGATTTTCCCCTGAGAATCTCTGAAGACTTATTCTTCCGTCACATATACAAAAGCAAGACTTCCAGGTAGGCCA  1699
GCTCACAAGCCCAGGCTGGAGATCCTAACTGAGAATTTCTACCTGTGTTCATTCTGTTCTACCTGTTCATTCTGTTCTACCTGTCTGAATCTGA   1789
TAGGAAAAGAAGGCTGCCTAAGGAGAGTTTTAGTATGTGGCTATCATGCAAGTGCTATGCCAAGCCATGTCTAAATGCTCTAAATGGCTTAATTA  1879
TATAGTAATGCACTCTCAGTAATGGGGACCAGCTTAAGTATAATTAAGTTAAGATGGTTAGTGGGTAATTCTGCTTCTAGTATTTTTTTTA      1969
CTGTGCATACAATGTTCATCGTATTTCCTTGGATTTCTGAATGCTGACCAGATATTGCACTAGGTCAAAACATTCAGTATAGC              2059
TGACATCTCCTATCACATTACAATACATCCCTCTTATAAGCCCCAGCTCTGCTTCTTCCACTGGCTCCACATCCACCCCAC                2149
TGGATCTTCAGAAGGCTAGAGGGCGACTCGGTGGTGCTTTTGTATGTTTCAATTAGGCTCTGAAATCTTGGGCAAAATGACAAGGGAG         2239
GGCCAGGATCCTCTCTCAGTGCACTCCAGTGTTACTTTCTCTCTTTTTTTTTGAGACAGGGTAAATATGACTCCTTTCTACTATGTTGCCCAGGCTGCTCTTGAA 2329
AGCACATTCTTAAAGGAAAAGTCAACATCTTCCCACCCTACCACAGCGTCCCGCGTAGCTGGCATACAGTGCAAGCCACTACAGTTCCAGCTAGCCAACTC   2419
TTCCTGGGCTCAAGCAGTCCTCCTTTTTTTTCTTTTTCTTTTGAGACGGCGCACCTCCTCAGCTCCAGCCCTATCACCCAGGCTGGAGTGGCACGATCTTGGCTCACTG 2509
CTCCTTGCCTGCTTCCTCCTGGTTCAAGCGATTCTCATGTCTCAGCCTCCAGTAGCTAGGACTACCGGCCGTGCACCACCATGCCCAGGCTAATT      2599
CAACCCTCTTCCTCCCTGGTTCAAGCGATTCATGTGGATTTCATCATGTTGGCCAGGCTGGTCTCGAACTCCTGACCTCAAGTGATCCACCTGCCT      2689
TTTATATTTTAGAATTTTAGAAGAGATGGCTAGGATTACAGGCATGAGCCACCGCCATTTATTTGAAAGTCCTTGTTTTTTGCTACTAATTATATAGTATACCATA  2779
TGGCCTCCCAAGGTGCTAGGATTACAGGCATGAGCCACCGCCCAAAAAAGCTGAAGCTAATCTTTGAAAAGAAAATATATATGTGCAGTATTTATTAAAGCAACATTTATTT 2869
TTCTGCCCACCCACCTACCCCCAAAAACAACCATCCTGCTCATAACATCTTTGAAAAGAAAATATATATGTGCAGTATTTATTAAAGCAACATTTATTT 2959
CATTATCATTCAAAACAACCATCCTGCTCATAACATCTTTGAAAAGAAAATATATATGTGCAGTATTTATTAAAGCAACATTTATTT           3049
AAGAATAAAGTCTTGTTAATTACTATATTTTAGATGCAATGTGATC                                                    3095
```

Fig. 2-2

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
( A ) LENGTH: 3095 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( A ) ORGANISM: Homo sapiens ( i x ) FEATURE:
( A ) NAME/KEY: CDS
( B ) LOCATION: 80..1151

( x i ) SEQUENCE DESCRIPTION: SEQ ID NO:1:

```
TAGCAGAGCA ATCACCACCA AGCCTGGAAT AACTGCAAGG GCTCTGCTGA CATCTTCCTG            60

AGGTGCCAAG GAAATGAGG ATG GAG GAA GGA ATG AAT GTT CTC CAT GAC TTT           112
                       Met Glu Glu Gly Met Asn Val Leu His Asp Phe
                         1               5                      10

GGG ATC CAG TCA ACA CAT TAC CTC CAG GTG AAT TAC CAA GAC TCC CAG            160
Gly Ile Gln Ser Thr His Tyr Leu Gln Val Asn Tyr Gln Asp Ser Gln
             15                  20                  25

GAC TGG TTC ATC TTG GTG TCC GTG ATC GCA GAC CTC AGG AAT GCC TTC            208
Asp Trp Phe Ile Leu Val Ser Val Ile Ala Asp Leu Arg Asn Ala Phe
         30                  35                  40

TAC GTC CTC TTC CCC ATC TGG TTC CAT CTT CAG GAA GCT GTG GGC ATT            256
Tyr Val Leu Phe Pro Ile Trp Phe His Leu Gln Glu Ala Val Gly Ile
     45                  50                  55

AAA CTC CTT TGG GTA GCT GTG ATT GGA GAC TGG CTC AAC CTC GTC TTT            304
Lys Leu Leu Trp Val Ala Val Ile Gly Asp Trp Leu Asn Leu Val Phe
 60                  65                  70                  75

AAG TGG ATT CTC TTT GGA CAG CGT CCA TAC TGG TGG GTT TTG GAT ACT            352
Lys Trp Ile Leu Phe Gly Gln Arg Pro Tyr Trp Trp Val Leu Asp Thr
                 80                  85                  90

GAC TAC TAC AGC AAC ACT TCC GTG CCC CTG ATA AAG CAG TTC CCT GTA            400
Asp Tyr Tyr Ser Asn Thr Ser Val Pro Leu Ile Lys Gln Phe Pro Val
                 95                 100                 105

ACC TGT GAG ACT GGA CCA GGG AGC CCC TCT GGC CAT GCC ATG GGC ACA            448
Thr Cys Glu Thr Gly Pro Gly Ser Pro Ser Gly His Ala Met Gly Thr
             110                 115                 120

GCA GGT GTA TAC TAC GTG ATG GTC ACA TCT ACT CTT TCC ATC TTT CAG            496
Ala Gly Val Tyr Tyr Val Met Val Thr Ser Thr Leu Ser Ile Phe Gln
     125                 130                 135

GGA AAG ATA AAG CCG ACC TAC AGA TTT CGG TGC TTG AAT GTC ATT TTG            544
Gly Lys Ile Lys Pro Thr Tyr Arg Phe Arg Cys Leu Asn Val Ile Leu
 140                 145                 150                 155

TGG TTG GGA TTC TGG GCT GTG CAG CTG AAT GTC TGT CTG TCA CGA ATC            592
Trp Leu Gly Phe Trp Ala Val Gln Leu Asn Val Cys Leu Ser Arg Ile
                 160                 165                 170

TAC CTT GCT GCT CAT TTT CCT CAT CAA GTT GTT GCT GGA GTC CTG TCA            640
Tyr Leu Ala Ala His Phe Pro His Gln Val Val Ala Gly Val Leu Ser
                 175                 180                 185

GGC ATT GCT GTT ACA GAA ACT TTC AGC CAC ATC CAC AGC ATC TAT AAT            688
Gly Ile Ala Val Thr Glu Thr Phe Ser His Ile His Ser Ile Tyr Asn
```

-continued

| | 190 | | | | | 195 | | | | | 200 | | | | |
|---|---|---|---|---|---|---|---|---|---|---|---|---|---|---|---|---|
| GCC | AGC | CTC | AAG | AAA | TAT | TTT | CTC | ATT | ACC | TTC | TTC | CTG | TTC | AGC | TTC | 736 |
| Ala | Ser | Leu | Lys | Lys | Tyr | Phe | Leu | Ile | Thr | Phe | Phe | Leu | Phe | Ser | Phe | |
| | 205 | | | | | 210 | | | | | 215 | | | | | |
| GCC | ATC | GGA | TTT | TAT | CTG | CTG | CTC | AAG | GGA | CTG | GGT | GTA | GAC | CTC | CTG | 784 |
| Ala | Ile | Gly | Phe | Tyr | Leu | Leu | Leu | Lys | Gly | Leu | Gly | Val | Asp | Leu | Leu | |
| 220 | | | | | 225 | | | | | 230 | | | | | 235 | |
| TGG | ACT | CTG | GAG | AAA | GCC | CAG | AGG | TGG | TGC | GAG | CAG | CCA | GAA | TGG | GTC | 832 |
| Trp | Thr | Leu | Glu | Lys | Ala | Gln | Arg | Trp | Cys | Glu | Gln | Pro | Glu | Trp | Val | |
| | | | | 240 | | | | | 245 | | | | | 250 | | |
| CAC | ATT | GAC | ACC | ACA | CCC | TTT | GCC | AGC | CTC | CTC | AAG | AAC | CTG | GGC | ACG | 880 |
| His | Ile | Asp | Thr | Thr | Pro | Phe | Ala | Ser | Leu | Leu | Lys | Asn | Leu | Gly | Thr | |
| | | | 255 | | | | | 260 | | | | | 265 | | | |
| CTC | TTT | GGC | CTG | GGG | CTG | GCT | CTC | AAC | TCC | AGC | ATG | TAC | AGG | GAG | AGC | 928 |
| Leu | Phe | Gly | Leu | Gly | Leu | Ala | Leu | Asn | Ser | Ser | Met | Tyr | Arg | Glu | Ser | |
| | | 270 | | | | | 275 | | | | | 280 | | | | |
| TGC | AAG | GGG | AAA | CTC | AGC | AAG | TGG | CTC | CCA | TTC | CGC | CTC | AGC | TCT | ATT | 976 |
| Cys | Lys | Gly | Lys | Leu | Ser | Lys | Trp | Leu | Pro | Phe | Arg | Leu | Ser | Ser | Ile | |
| | 285 | | | | | 290 | | | | | 295 | | | | | |
| GTA | GCC | TCC | CTC | GTC | CTC | CTG | CAC | GTC | TTT | GAC | TCC | TTG | AAA | CCC | CCA | 1024 |
| Val | Ala | Ser | Leu | Val | Leu | Leu | His | Val | Phe | Asp | Ser | Leu | Lys | Pro | Pro | |
| 300 | | | | | 305 | | | | | 310 | | | | | 315 | |
| TCC | CAA | GTC | GAG | CTG | GTC | TTC | TAC | GTC | TTG | TCC | TTC | TGC | AAG | AGT | GCG | 1072 |
| Ser | Gln | Val | Glu | Leu | Val | Phe | Tyr | Val | Leu | Ser | Phe | Cys | Lys | Ser | Ala | |
| | | | | 320 | | | | | 325 | | | | | 330 | | |
| GTA | GTG | CCC | CTG | GCA | TCC | GTC | AGT | GTC | ATC | CCC | TAC | TGC | CTC | GCC | CAG | 1120 |
| Val | Val | Pro | Leu | Ala | Ser | Val | Ser | Val | Ile | Pro | Tyr | Cys | Leu | Ala | Gln | |
| | | | 335 | | | | | 340 | | | | | 345 | | | |
| GTC | CTG | GGC | CAG | CCG | CAC | AAG | AAG | TCG | TTG | T | AAGAGATGTG | GAGTCTTCGG | | | | 1171 |
| Val | Leu | Gly | Gln | Pro | His | Lys | Lys | Ser | Leu | | | | | | | |
| | | 350 | | | | | 355 | | | | | | | | | |

TGTTTAAAGT CAACAACCAT GCCAGGGATT GAGGAGGACT ACTATTTGAA GCAATGGGCA 1231

CTGGTATTTG GAGCAAGTGA CATGCCATCC ATTCTGCCGT CGTGGAATTA AATCACGGAT 1291

GGCAGATTGG AGGGTCGCCT GGCTTATTCC CATGTGTGAC TCCAGCCTGC CCTCAGCACA 1351

GACTCTTTCA GATGGAGGTG CCATATCACG TACACCATAT GCAAGTTTCC CGCCAGGAGG 1411

TCCTCCTCTC TCTACTTGAA TACTCTCACA AGTAGGGAGC TCACTCCCAC TGGAACAGCC 1471

CATTTTATCT TTGAATGGTC TTCTGCCAGC CCATTTTGAG GCCAGAGGTG CTGTCAGCTC 1531

AGGTGGTCCT CTTTTACAAT CCTAATCATA TTGGGTAATG TTTTTGAAAA GCTAATGAAG 1591

CTATTGAGAA AGACCTGTTG CTAGAAGTTG GGTTGTTCTG GATTTTCCCC TGAAGACTTA 1651

CTTATTCTTC CGTCACATAT ACAAAAGCAA GACTTCCAGG TAGGGCCAGC TCACAAGCCC 1711

AGGCTGGAGA TCCTAACTGA GAATTTTCTA CCTGTGTTCA TTCTTACCGA GAAAAGGAGA 1771

AAGGAGCTCT GAATCTGATA GGAAAAGAAG GCTGCCTAAG GAGGAGTTTT TAGTATGTGG 1831

CGTATCATGC AAGTGCTATG CCAAGCCATG TCTAAATGGC TTTAATTATA TAGTAATGCA 1891

CTCTCAGTAA TGGGGGACCA GCTTAAGTAT AATTAATAGA TGGTTAGTGG GGTAATTCTG 1951

CTTCTAGTAT TTTTTTTACT GTGCATACAT GTTCATCGTA TTTCCTTGGA TTTCTGAATG 2011

GCTGCAGTGA CCCAGATATT GCACTAGGTC AAAACATTCA GGTATAGCTG ACATCTCCTC 2071

TATCACATTA CATCATCCTC CTTATAAGCC CAGCTCTGCT TTTTCCAGAT TCTTCCACTG 2131

GCTCCACATC CACCCCACTG GATCTTCAGA AGGCTAGAGG GCGACTCTGG TGGTGCTTTT 2191

GTATGTTTCA ATTAGGCTCT GAAATCTTGG GCAAAATGAC AAGGGGAGGG CCAGGATTCC 2251

TCTCTCAGGT CACTCCAGTG TTACTTTTAA TTCCTAGAGG GTAAATATGA CTCCTTTCTC 2311

```
TATCCCAAGC CAACCAAGAG CACATTCTTA AAGGAAAAGT CAACATCTTC TCTCTTTTTT    2371
TTTTTTTTTG AGACAGGGTC TCACTATGTT GCCCAGGCTG CTCTTGAATT CCTGGGCTCA    2431
AGCAGTCCTC CCACCCTACC ACAGCGTCCC GCGTAGCTGG CATACAGGTG CAAGCCACTA    2491
TGTCCAGCTA GCCAACTCCT CCTTGCCTGC TTTTCTTTTT TTTTCTTTTT TTGAGACGGC    2551
GCACCTATCA CCCAGGCTGG AGTGGAGTGG CACGATCTTG GCTCACTGCA ACCTCTTCCT    2611
CCTGGTTCAA GCGATTCTCA TGTCTCAGCC TCCTCAGTAG CTAGGACTAC CGGCGTGCAC    2671
CACCATGCCA GGCTAATTTT TATATTTTTA GAATTTAGA AGAGATGGGA TTTCATCATG     2731
TTGGCCAGGC TGGTCTCGAA CTCCTGACCT CAAGTGATCC ACCTGCCTTG GCCTCCCAAG    2791
GTGCTAGGAT TACAGGCATG AGCCACCGCA CCGGGCCCTC CTTGCCTGTT TTTCAATCTC    2851
ATCTGATATG CAGAGTATTT CTGCCCCACC CACCTACCCC CCAAAAAAAG CTGAAGCCTA    2911
TTTATTTGAA AGTCCTTGTT TTTGCTACTA ATTATATAGT ATACCATACA TTATCATTCA    2971
AAACAACCAT CCTGCTCATA ACATCTTTGA AAAGAAAAAT ATATATGTGC AGTATTTTAT    3031
TAAAGCAACA TTTTATTTAA GAATAAAGTC TTGTTAATTA CTATATTTTA GATGCAATGT    3091
GATC                                                                 3095
```

(2) INFORMATION FOR SEQ ID NO:2:

(i) SEQUENCE CHARACTERISTICS:
  (A) LENGTH: 357 amino acids
  (B) TYPE: amino acid
  (D) TOPOLOGY: linear (ii) MOLECULE TYPE: protein (xi) SEQUENCE DESCRIPTION: SEQ ID NO:2:

```
Met Glu Glu Gly Met Asn Val Leu His Asp Phe Gly Ile Gln Ser Thr
 1               5                  10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
    50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
    130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Thr
            180                 185                 190

Glu Thr Phe Ser His Ile His Ser Ile Tyr Asn Ala Ser Leu Lys Lys
        195                 200                 205
```

Tyr Phe Leu Ile Thr Phe Phe Leu Phe Ser Phe Ala Ile Gly Phe Tyr
    210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
            245                 250                 255

Pro Phe Ala Ser Leu Leu Lys Asn Leu Gly Thr Leu Phe Gly Leu Gly
            260                 265                 270

Leu Ala Leu Asn Ser Ser Met Tyr Arg Glu Ser Cys Lys Gly Lys Leu
        275                 280                 285

Ser Lys Trp Leu Pro Phe Arg Leu Ser Ser Ile Val Ala Ser Leu Val
    290                 295                 300

Leu Leu His Val Phe Asp Ser Leu Lys Pro Pro Ser Gln Val Glu Leu
305                 310                 315                 320

Val Phe Tyr Val Leu Ser Phe Cys Lys Ser Ala Val Val Pro Leu Ala
                325                 330                 335

Ser Val Ser Val Ile Pro Tyr Cys Leu Ala Gln Val Leu Gly Gln Pro
            340                 345                 350

His Lys Lys Ser Leu
            355

( 2 ) INFORMATION FOR SEQ ID NO:3:

( i ) SEQUENCE CHARACTERISTICS:
        ( A ) LENGTH: 129 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( i x ) FEATURE:
        ( A ) NAME/KEY: Modified-site
        ( B ) LOCATION: 1..129
        ( D ) OTHER INFORMATION: /label=Truncated Pro
            / note="Shortened G-6-Pase protein due to TA
            insertion at nucleotide 459 of the wild-type"

( x i ) SEQUENCE DESCRIPTION: SEQ ID NO:3:

Met Glu Glu Gly Met Asn Val Leu His Asp Phe Gly Ile Gln Ser Thr
1               5                   10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
            35                  40                  45

Ile Trp Phe His Leu Gln Glu Ala Val Gly Ile Lys Leu Leu Trp Val
        50                  55                  60

Ala Val Ile Gly Asp Trp Leu Asn Leu Val Phe Lys Trp Ile Leu Phe
65                  70                  75                  80

Gly Gln Arg Pro Tyr Trp Trp Val Leu Asp Thr Asp Tyr Tyr Ser Asn
            85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val (2) INFORMATION FOR SEQ ID NO:4:

(i) SEQUENCE CHARACTERISTICS:
        (A) LENGTH: 357 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (ix) FEATURE:
        (A) NAME/KEY: Modified-site
        (B) LOCATION: 1..357
        (D) OTHER INFORMATION: /label=R to C at 83
        / note="The G-6-Pase amino acid sequence mutated
        from Arg to Cys at position 83."

(xi) SEQUENCE DESCRIPTION: SEQ ID NO:4:

```
Met Glu Glu Gly Met Asn Val Leu His Asp Phe Gly Ile Gln Ser Thr
 1               5                  10                  15

His Tyr Leu Gln Val Asn Tyr Gln Asp Ser Gln Asp Trp Phe Ile Leu
            20                  25                  30

Val Ser Val Ile Ala Asp Leu Arg Asn Ala Phe Tyr Val Leu Phe Pro
        35                  40                  45

Ile Trp Phe His Leu Gln Glu Ala Val Gly Ile Lys Leu Leu Trp Val
50                  55                  60

Ala Val Ile Gly Asp Trp Leu Asn Leu Val Phe Lys Trp Ile Leu Phe
65                  70                  75                  80

Gly Gln Cys Pro Tyr Trp Trp Val Leu Asp Thr Asp Tyr Tyr Ser Asn
                85                  90                  95

Thr Ser Val Pro Leu Ile Lys Gln Phe Pro Val Thr Cys Glu Thr Gly
            100                 105                 110

Pro Gly Ser Pro Ser Gly His Ala Met Gly Thr Ala Gly Val Tyr Tyr
        115                 120                 125

Val Met Val Thr Ser Thr Leu Ser Ile Phe Gln Gly Lys Ile Lys Pro
130                 135                 140

Thr Tyr Arg Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Thr
            180                 185                 190

Glu Thr Phe Ser His Ile His Ser Ile Tyr Asn Ala Ser Leu Lys Lys
        195                 200                 205

Tyr Phe Leu Ile Thr Phe Phe Leu Phe Ser Phe Ala Ile Gly Phe Tyr
210                 215                 220

Leu Leu Leu Lys Gly Leu Gly Val Asp Leu Leu Trp Thr Leu Glu Lys
225                 230                 235                 240

Ala Gln Arg Trp Cys Glu Gln Pro Glu Trp Val His Ile Asp Thr Thr
                245                 250                 255

Pro Phe Ala Ser Leu Leu Lys Asn Leu Gly Thr Leu Phe Gly Leu Gly
            260                 265                 270
```

|     |     |     |     |     |     |     |     |     |     |     |     |     |     |     |
|-----|-----|-----|-----|-----|-----|-----|-----|-----|-----|-----|-----|-----|-----|-----|
| Leu | Ala | Leu | Asn | Ser | Ser | Met | Tyr | Arg | Glu | Ser | Cys | Lys | Gly | Lys | Leu |
|     |     | 275 |     |     |     | 280 |     |     |     |     | 285 |     |     |     |
| Ser | Lys | Trp | Leu | Pro | Phe | Arg | Leu | Ser | Ser | Ile | Val | Ala | Ser | Leu | Val |
|     | 290 |     |     |     |     | 295 |     |     |     |     | 300 |     |     |     |
| Leu | Leu | His | Val | Phe | Asp | Ser | Leu | Lys | Pro | Pro | Ser | Gln | Val | Glu | Leu |
| 305 |     |     |     |     | 310 |     |     |     |     | 315 |     |     |     |     | 320 |
| Val | Phe | Tyr | Val | Leu | Ser | Phe | Cys | Lys | Ser | Ala | Val | Val | Pro | Leu | Ala |
|     |     |     |     | 325 |     |     |     |     | 330 |     |     |     |     | 335 |     |
| Ser | Val | Ser | Val | Ile | Pro | Tyr | Cys | Leu | Ala | Gln | Val | Leu | Gly | Gln | Pro |
|     |     |     | 340 |     |     |     |     | 345 |     |     |     |     | 350 |     |     |
| His | Lys | Lys | Ser | Leu |
|     |     | 355 |     |     |

( 2 ) INFORMATION FOR SEQ ID NO:5:

( i ) SEQUENCE CHARACTERISTICS:
           ( A ) LENGTH: 346 amino acids
           ( B ) TYPE: amino acid
           ( C ) STRANDEDNESS: single
           ( D ) TOPOLOGY: linear ( i i ) MOLECULE TYPE: protein ( i i i ) HYPOTHETICAL: NO ( v i ) ORIGINAL SOURCE:
           ( A ) ORGANISM: Homo sapiens ( i x ) FEATURE:
           ( A ) NAME/KEY: Modified-site
           ( B ) LOCATION: 1..346
           ( D ) OTHER INFORMATION: /label=Truncated prot
              / note="G-6-Pase truncated due to a C to T
              mutation at nucleotide 1118 converting a glutamine
              to a stop codon at 347"

( x i ) SEQUENCE DESCRIPTION: SEQ ID NO:5:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Glu | Glu | Gly | Met | Asn | Val | Leu | His | Asp | Phe | Gly | Ile | Gln | Ser | Thr |
| 1   |     |     |     | 5   |     |     |     |     | 10  |     |     |     |     | 15  |     |
| His | Tyr | Leu | Gln | Val | Asn | Tyr | Gln | Asp | Ser | Gln | Asp | Trp | Phe | Ile | Leu |
|     |     |     | 20  |     |     |     | 25  |     |     |     |     | 30  |     |     |     |
| Val | Ser | Val | Ile | Ala | Asp | Leu | Arg | Asn | Ala | Phe | Tyr | Val | Leu | Phe | Pro |
|     |     | 35  |     |     |     |     | 40  |     |     |     |     | 45  |     |     |     |
| Ile | Trp | Phe | His | Leu | Gln | Glu | Ala | Val | Gly | Ile | Lys | Leu | Leu | Trp | Val |
|     | 50  |     |     |     |     | 55  |     |     |     |     | 60  |     |     |     |     |
| Ala | Val | Ile | Gly | Asp | Trp | Leu | Asn | Leu | Val | Phe | Lys | Trp | Ile | Leu | Phe |
| 65  |     |     |     |     | 70  |     |     |     |     | 75  |     |     |     |     | 80  |
| Gly | Gln | Arg | Pro | Tyr | Trp | Trp | Val | Leu | Asp | Thr | Asp | Tyr | Tyr | Ser | Asn |
|     |     |     |     | 85  |     |     |     |     | 90  |     |     |     |     | 95  |     |
| Thr | Ser | Val | Pro | Leu | Ile | Lys | Gln | Phe | Pro | Val | Thr | Cys | Glu | Thr | Gly |
|     |     |     | 100 |     |     |     |     | 105 |     |     |     |     | 110 |     |     |
| Pro | Gly | Ser | Pro | Ser | Gly | His | Ala | Met | Gly | Thr | Ala | Gly | Val | Tyr | Tyr |
|     |     | 115 |     |     |     |     | 120 |     |     |     |     | 125 |     |     |     |
| Val | Met | Val | Thr | Ser | Thr | Leu | Ser | Ile | Phe | Gln | Gly | Lys | Ile | Lys | Pro |
|     | 130 |     |     |     |     | 135 |     |     |     |     | 140 |     |     |     |     |
| Thr | Tyr | Arg | Phe | Arg | Cys | Leu | Asn | Val | Ile | Leu | Trp | Leu | Gly | Phe | Trp |
| 145 |     |     |     |     | 150 |     |     |     |     | 155 |     |     |     |     | 160 |
| Ala | Val | Gln | Leu | Asn | Val | Cys | Leu | Ser | Arg | Ile | Tyr | Leu | Ala | Ala | His |
|     |     |     |     | 165 |     |     |     |     | 170 |     |     |     |     | 175 |     |
| Phe | Pro | His | Gln | Val | Val | Ala | Gly | Val | Leu | Ser | Gly | Ile | Ala | Val | Thr |
|     |     |     | 180 |     |     |     |     | 185 |     |     |     |     | 190 |     |     |

```
Glu  Thr  Phe  Ser  His  Ile  His  Ser  Ile  Tyr  Asn  Ala  Ser  Leu  Lys  Lys
          195                      200                      205

Tyr  Phe  Leu  Ile  Thr  Phe  Phe  Leu  Phe  Ser  Phe  Ala  Ile  Gly  Phe  Tyr
     210                      215                      220

Leu  Leu  Leu  Lys  Gly  Leu  Gly  Val  Asp  Leu  Leu  Trp  Thr  Leu  Glu  Lys
225                      230                      235                      240

Ala  Gln  Arg  Trp  Cys  Glu  Gln  Pro  Glu  Trp  Val  His  Ile  Asp  Thr  Thr
               245                      250                      255

Pro  Phe  Ala  Ser  Leu  Leu  Lys  Asn  Leu  Gly  Thr  Leu  Phe  Gly  Leu  Gly
               260                      265                      270

Leu  Ala  Leu  Asn  Ser  Ser  Met  Tyr  Arg  Glu  Ser  Cys  Lys  Gly  Lys  Leu
          275                      280                      285

Ser  Lys  Trp  Leu  Pro  Phe  Arg  Leu  Ser  Ser  Ile  Val  Ala  Ser  Leu  Val
     290                      295                      300

Leu  Leu  His  Val  Phe  Asp  Ser  Leu  Lys  Pro  Pro  Ser  Gln  Val  Glu  Leu
305                      310                      315                      320

Val  Phe  Tyr  Val  Leu  Ser  Phe  Cys  Lys  Ser  Ala  Val  Val  Pro  Leu  Ala
               325                      330                      335

Ser  Val  Ser  Val  Ile  Pro  Tyr  Cys  Leu  Ala
               340                      345
```

(2) INFORMATION FOR SEQ ID NO:6:

( i ) SEQUENCE CHARACTERISTICS:
        ( A ) LENGTH: 357 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v i ) ORIGINAL SOURCE:
        ( A ) ORGANISM: Homo sapiens ( i x ) FEATURE:
        ( A ) NAME/KEY: Modified-site
        ( B ) LOCATION: 1..357
        ( D ) OTHER INFORMATION: /label=R to C at 295
        / note="G-6-Pase Mutated at position 295 with Arg
        changed to Cys"

( x i ) SEQUENCE DESCRIPTION: SEQ ID NO:6:

```
Met  Glu  Glu  Gly  Met  Asn  Val  Leu  His  Asp  Phe  Gly  Ile  Gln  Ser  Thr
1                   5                        10                       15

His  Tyr  Leu  Gln  Val  Asn  Tyr  Gln  Asp  Ser  Gln  Asp  Trp  Phe  Ile  Leu
          20                       25                       30

Val  Ser  Val  Ile  Ala  Asp  Leu  Arg  Asn  Ala  Phe  Tyr  Val  Leu  Phe  Pro
          35                       40                       45

Ile  Trp  Phe  His  Leu  Gln  Glu  Ala  Val  Gly  Ile  Lys  Leu  Leu  Trp  Val
     50                       55                       60

Ala  Val  Ile  Gly  Asp  Trp  Leu  Asn  Leu  Val  Phe  Lys  Trp  Ile  Leu  Phe
65                       70                       75                       80

Gly  Gln  Arg  Pro  Tyr  Trp  Trp  Val  Leu  Asp  Thr  Asp  Tyr  Tyr  Ser  Asn
               85                       90                       95

Thr  Ser  Val  Pro  Leu  Ile  Lys  Gln  Phe  Pro  Val  Thr  Cys  Glu  Thr  Gly
               100                      105                      110

Pro  Gly  Ser  Pro  Ser  Gly  His  Ala  Met  Gly  Thr  Ala  Gly  Val  Tyr  Tyr
          115                      120                      125
```

```
Val  Met  Val  Thr  Ser  Thr  Leu  Ser  Ile  Phe  Gln  Gly  Lys  Ile  Lys  Pro
     130            135                      140
Thr  Tyr  Arg  Phe  Arg  Cys  Leu  Asn  Val  Ile  Leu  Trp  Leu  Gly  Phe  Trp
145                      150                      155                      160
Ala  Val  Gln  Leu  Asn  Val  Cys  Leu  Ser  Arg  Ile  Tyr  Leu  Ala  Ala  His
               165                      170                      175
Phe  Pro  His  Gln  Val  Val  Ala  Gly  Val  Leu  Ser  Gly  Ile  Ala  Val  Thr
               180                      185                      190
Glu  Thr  Phe  Ser  His  Ile  His  Ser  Ile  Tyr  Asn  Ala  Ser  Leu  Lys  Lys
          195                      200                      205
Tyr  Phe  Leu  Ile  Thr  Phe  Phe  Leu  Phe  Ser  Phe  Ala  Ile  Gly  Phe  Tyr
     210                      215                      220
Leu  Leu  Leu  Lys  Gly  Leu  Gly  Val  Asp  Leu  Leu  Trp  Thr  Leu  Glu  Lys
225                      230                      235                      240
Ala  Gln  Arg  Trp  Cys  Glu  Gln  Pro  Glu  Trp  Val  His  Ile  Asp  Thr  Thr
               245                      250                      255
Pro  Phe  Ala  Ser  Leu  Leu  Lys  Asn  Leu  Gly  Thr  Leu  Phe  Gly  Leu  Gly
               260                      265                      270
Leu  Ala  Leu  Asn  Ser  Ser  Met  Tyr  Arg  Glu  Ser  Cys  Lys  Gly  Lys  Leu
          275                      280                      285
Ser  Lys  Trp  Leu  Pro  Phe  Cys  Leu  Ser  Ser  Ile  Val  Ala  Ser  Leu  Val
     290                      295                      300
Leu  Leu  His  Val  Phe  Asp  Ser  Leu  Lys  Pro  Pro  Ser  Gln  Val  Glu  Leu
305                      310                      315                      320
Val  Phe  Tyr  Val  Leu  Ser  Phe  Cys  Lys  Ser  Ala  Val  Pro  Leu  Ala
                    325                      330                      335
Ser  Val  Ser  Val  Ile  Pro  Tyr  Cys  Leu  Ala  Gln  Val  Leu  Gly  Gln  Pro
               340                      345                      350
His  Lys  Lys  Ser  Leu
          355
```

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

AAGGATGGAG GAAGGAATGA A          21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

GCCTTACAAA GACTTCTTGT G          21

(2) INFORMATION FOR SEQ ID NO:9:

(i) SEQUENCE CHARACTERISTICS:
        (A) LENGTH: 82 base pairs
        (B) TYPE: nucleic acid
        (C) STRANDEDNESS: single ( D ) TOPOLOGY: linear ( x i ) SEQUENCE DESCRIPTION: SEQ ID NO:9:

TAGCAGAGCA ATCACCACCA AGCCTGGAAT AACTGCAAGG GCTCTGCTGA CATCTTCCTG        60

AGGTGCCAAG GAAATGAGGA TG        82

( 2 ) INFORMATION FOR SEQ ID NO:10:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

GTAAGAACCA TATAGAGAGG AGATCAGCAA GAAAAGAGGC TGGCATT        47

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TCTGCTGACA TCTTCCT        17

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCCTCTTTTC TTGCTG        16

( 2 ) INFORMATION FOR SEQ ID NO:13:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

AAAAGCATTC ATTCAGTAAC CCCAGAAACT TGTTCTGTTT TTCCATAG        48

( 2 ) INFORMATION FOR SEQ ID NO:14:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTAAGCGTCC CAGCCCCTGC AGACAGAAGC TGAGTGGACC TCGTTT        46

( 2 ) INFORMATION FOR SEQ ID NO:15:

( i ) SEQUENCE CHARACTERISTICS:
        ( A ) LENGTH: 18 base pairs
        ( B ) TYPE: nucleic acid (C) STRANDEDNESS: single
(D) TOPOLOGY: linear (xi) SEQUENCE DESCRIPTION: SEQ ID NO:15:

GCATTCATTC AGTAACCC                                                    18

(2) INFORMATION FOR SEQ ID NO:16:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:16:

TCCACTCAGC TTCTGTCTG                                                   19

(2) INFORMATION FOR SEQ ID NO:17:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:17:

CTTTTCACCT TTACTCCATT CTCTTTCCTG CCCTTTAG                               38

(2) INFORMATION FOR SEQ ID NO:18:

(i) SEQUENCE CHARACTERISTICS:
(A) LENGTH: 79 base pairs
(B) TYPE: nucleic acid
(C) STRANDEDNESS: single
(D) TOPOLOGY: linear (xi) SEQUENCE DESCRIPTION: SEQ ID NO:18:

GTAAGAACTC ACCACTGGGG TGTAGGTGGT GGAGGGCAGG AGGCAGCTCT CTCTGTAGCT       60

GACACACCAC GTATCTTCC                                                   79

(2) INFORMATION FOR SEQ ID NO:19:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:19:

CACCTTTACT CCATTCTC                                                    18

(2) INFORMATION FOR SEQ ID NO:20:

(i) SEQUENCE CHARACTERISTICS:
(A) LENGTH: 17 base pairs
(B) TYPE: nucleic acid
(C) STRANDEDNESS: single
(D) TOPOLOGY: linear (xi) SEQUENCE DESCRIPTION: SEQ ID NO:20:

GTGGTGTGTC AGCTACA                                                     17

(2) INFORMATION FOR SEQ ID NO:21:

(i) SEQUENCE CHARACTERISTICS:
(A) LENGTH: 92 base pairs ( B ) TYPE: nucleic acid
( C ) STRANDEDNESS: single
( D ) TOPOLOGY: linear ( x i ) SEQUENCE DESCRIPTION: SEQ ID NO:21:

```
AGTTTGCCAG GCTCCAACAT TTCTGCAGGG GCTGTTTTCT TTGCTGAAGG ATCTGCACCT    60
GTGTTCTGTT ATGGTTGCCT CTTCTGTTGC AG                                  92
```

( 2 ) INFORMATION FOR SEQ ID NO:22:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

```
GTATGGGCTG ATCTGACTCC CTTCCTTCTC CCCCAAACCC CATTCCGTTT CTCTCCCTAA    60
TCAGGA                                                               66
```

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

```
GCCAGGCTCC AACATTT                                                   17
```

( 2 ) INFORMATION FOR SEQ ID NO:24:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

```
GGAGAGAAAC GGAATGG                                                   17
```

( 2 ) INFORMATION FOR SEQ ID NO:25:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

```
GTCCCAAATC CTTCCTATCT CTCACAGTCA TGCTTTCTTC CACTCAG                  47
```

( 2 ) INFORMATION FOR SEQ ID NO:26:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
TAAGAGATGT GGAGTCTTCG GTGTTTAAAG TCAACAACCA TGCCAGGGAT TGAGGAGGAC    60
TACTATTTGA AGCAATGGGC ACTGGTATTT GGAGCAAGTG A                       101
```

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

CTTCCTATCT CTCACAG 17

( 2 ) INFORMATION FOR SEQ ID NO:28:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

TCACTTGCTC CAAATACC 18

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

AGGATGGAGG AAGGAATGAA 20

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

TTACAACGAC TTCTTGTGCG GCTG 24

( 2 ) INFORMATION FOR SEQ ID NO:31:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

TGGACAGTGT CCATACTGGT GG 22

( 2 ) INFORMATION FOR SEQ ID NO:32:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCACCAGTAT GGACACTGTC CA 22

( 2 ) INFORMATION FOR SEQ ID NO:33:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

```
GCTCCCATTC TGCCTCAGCT C                                                   21
```

( 2 ) INFORMATION FOR SEQ ID NO:34:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

```
GAGCTGAGGC AGAATGGGAG C                                                   21
```

( 2 ) INFORMATION FOR SEQ ID NO:35:

( i ) SEQUENCE CHARACTERISTICS:
        ( A ) LENGTH: 2259 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Murine ( i x ) FEATURE:
        ( A ) NAME/KEY: CDS
        ( B ) LOCATION: 83..1156

( x i ) SEQUENCE DESCRIPTION: SEQ ID NO:35:

```
AGCAGAGGGA  TCGGGGCCAA  CCGGGCTTGG  ACTCACTGCA  CGGGCTCTGC  TGGCAGCTTC          60

CTGAGGTACC  AAGGGAGGAA  GG ATG GAG GAA GGA ATG AAC ATT CTC CAT GAC           112
                          Met Glu Glu Gly Met Asn Ile Leu His Asp
                           1               5                  10

TTT GGG ATC CAG TCG ACT CGC TAT CTC CAA GTG AAT TAC CAA GAC TCC             160
Phe Gly Ile Gln Ser Thr Arg Tyr Leu Gln Val Asn Tyr Gln Asp Ser
             15                  20                  25

CAG GAC TGG TTC ATC CTT GTG TCT GTG ATT GCT GAC CTG AGG AAC GCC             208
Gln Asp Trp Phe Ile Leu Val Ser Val Ile Ala Asp Leu Arg Asn Ala
         30                  35                  40

TTC TAT GTC CTC TTT CCC ATC TGG TTC CAT CTT AAA GAG ACT GTG GGC             256
Phe Tyr Val Leu Phe Pro Ile Trp Phe His Leu Lys Glu Thr Val Gly
             45                  50                  55

ATC AAT CTC CTC TGG GTG GCA GTG GTC GGA GAC TGG TTC AAC CTC GTC             304
Ile Asn Leu Leu Trp Val Ala Val Val Gly Asp Trp Phe Asn Leu Val
     60                  65                  70

TTC AAG TGG ATT CTG TTT GGA CAA CGC CCG TAT TGG TGG GTC CTG GAC             352
Phe Lys Trp Ile Leu Phe Gly Gln Arg Pro Tyr Trp Trp Val Leu Asp
 75                  80                  85                  90

ACC GAC TAC TAC AGC AAC AGC TCC GTG CCT ATA ATA AAG CAG TTC CCT             400
Thr Asp Tyr Tyr Ser Asn Ser Ser Val Pro Ile Ile Lys Gln Phe Pro
             95                  100                 105

GTC ACC TGT GAG ACC GGA CCA GGA AGT CCC TCT GGC CAT GCC ATG GGC             448
Val Thr Cys Glu Thr Gly Pro Gly Ser Pro Ser Gly His Ala Met Gly
```

```
                        110                          115                          120
GCA  GCA  GGT  GTA  TAC  TAT  GTT  ATG  GTC  ACT  TCT  ACT  CTT  GCT  ATC  TTT            496
Ala  Ala  Gly  Val  Tyr  Tyr  Val  Met  Val  Thr  Ser  Thr  Leu  Ala  Ile  Phe
          125                      130                      135

CGA  GGA  AAG  AAA  AAG  CCA  ACG  TAT  GGA  TTC  CGG  TGT  TTG  AAC  GTC  ATC            544
Arg  Gly  Lys  Lys  Lys  Pro  Thr  Tyr  Gly  Phe  Arg  Cys  Leu  Asn  Val  Ile
          140                      145                      150

TTG  TGG  TTG  GGA  TTC  TGG  GCT  GTG  CAG  CTG  AAC  GTC  TGT  CTG  TCC  CGG            592
Leu  Trp  Leu  Gly  Phe  Trp  Ala  Val  Gln  Leu  Asn  Val  Cys  Leu  Ser  Arg
155                      160                      165                      170

ATC  TAC  CTT  GCT  GCT  CAC  TTT  CCC  CAC  CAG  GTC  GTG  GCT  GGA  GTC  TTG            640
Ile  Tyr  Leu  Ala  Ala  His  Phe  Pro  His  Gln  Val  Val  Ala  Gly  Val  Leu
                    175                      180                      185

TCA  GGC  ATT  GCT  GTG  GCT  GAA  ACT  TTC  AGC  CAC  ATC  CGG  GGC  ATC  TAC            688
Ser  Gly  Ile  Ala  Val  Ala  Glu  Thr  Phe  Ser  His  Ile  Arg  Gly  Ile  Tyr
               190                      195                      200

AAT  GCC  AGC  CTC  CGG  AAG  TAT  TGT  CTC  ATC  ACC  ATC  TTC  TTG  TTT  GGT            736
Asn  Ala  Ser  Leu  Arg  Lys  Tyr  Cys  Leu  Ile  Thr  Ile  Phe  Leu  Phe  Gly
          205                      210                      215

TTC  GCG  CTT  GGA  TTC  TAC  CTG  CTA  CTA  AAA  GGG  CTA  GGG  GTG  GAC  CTC            784
Phe  Ala  Leu  Gly  Phe  Tyr  Leu  Leu  Leu  Lys  Gly  Leu  Gly  Val  Asp  Leu
     220                      225                      230

CTG  TGG  ACT  TTG  GAG  AAA  GCC  AAG  AGA  TGG  TGT  GAG  CGG  CCA  GAA  TGG            832
Leu  Trp  Thr  Leu  Glu  Lys  Ala  Lys  Arg  Trp  Cys  Glu  Arg  Pro  Glu  Trp
235                      240                      245                      250

GTC  CAC  CTT  GAC  ACT  ACA  CCC  TTT  GCC  AGC  CTC  TTC  AAA  AAC  CTG  GGA            880
Val  His  Leu  Asp  Thr  Thr  Pro  Phe  Ala  Ser  Leu  Phe  Lys  Asn  Leu  Gly
                    255                      260                      265

ACC  CTC  TTG  GGG  TTG  GGG  CTG  GCC  CTC  AAC  TCC  AGC  ATG  TAC  CGG  AAG            928
Thr  Leu  Leu  Gly  Leu  Gly  Leu  Ala  Leu  Asn  Ser  Ser  Met  Tyr  Arg  Lys
               270                      275                      280

AGC  TGC  AAG  GGA  GAA  CTC  AGC  AAG  TCG  TTC  CCA  TTC  CGC  TTC  GCC  TGC            976
Ser  Cys  Lys  Gly  Glu  Leu  Ser  Lys  Ser  Phe  Pro  Phe  Arg  Phe  Ala  Cys
          285                      290                      295

ATT  GTG  GCT  TCC  TTG  GTC  CTC  CTG  CAT  CTC  TTT  GAC  TCT  CTG  AAG  CCC           1024
Ile  Val  Ala  Ser  Leu  Val  Leu  Leu  His  Leu  Phe  Asp  Ser  Leu  Lys  Pro
     300                      305                      310

CCA  TCC  CAG  GTT  GAG  TTG  ATC  TTC  TAC  ATC  TTG  TCT  TTC  TGC  AAG  AGC           1072
Pro  Ser  Gln  Val  Glu  Leu  Ile  Phe  Tyr  Ile  Leu  Ser  Phe  Cys  Lys  Ser
315                      320                      325                      330

GCA  ACA  GTT  CCC  TTT  GCA  TCT  GTC  AGT  CTT  ATC  CCA  TAC  TGC  CTA  GCC           1120
Ala  Thr  Val  Pro  Phe  Ala  Ser  Val  Ser  Leu  Ile  Pro  Tyr  Cys  Leu  Ala
                    335                      340                      345

CGG  ATC  CTG  GGA  CAG  ACA  CAC  AAG  AAG  TCT  TTG  TAAGGCATGC  AGAGTCTTTG           1173
Arg  Ile  Leu  Gly  Gln  Thr  His  Lys  Lys  Ser  Leu
               350                      355

GTATTTAAAG  TCAACCGCCA  TGCAAAGGAC  TAGGAACAAC  TAAAGCCTCT  GAAACCCATT                  1233

GTGAGGCCAG  AGGTGTTGAC  ATCGGCCCTG  GTAGCCCTGT  CTTTCTTTGC  TATCTTAACC                  1293

AAAAGGTGAA  TTTTTACAAA  GCTTACAGGG  CTGTTTGAGG  AAAGTGTGAA  TGCTGGAAAC                  1353

TGAGTCATTC  TGGATGGTTC  CCTGAAGATT  CGCTTACCAG  CCTCCTGTCA  GATACAGAAG                  1413

AGCAAGCCCA  GGCTAGAGAT  CCCAACTGAG  AATGCTCTTG  CGGTGCAGAA  TCTTCCGGCT                  1473

GGGAAAAGGA  AAAGAGCACC  ATGCATTTGC  CAGGAAGAGA  AAGAAGGATC  GGGAGGAGGG                  1533

AGAGTGTTTT  ATGTATCGAG  CAAACCAGAT  GCAATCTATG  TCTAACCGGC  TTCAGTTGTG                  1593

TCTGCGTCTT  TAGATACGAC  ACACTCAATA  ATAATAATAG  ACCAACTAGT  GTAATGAGTA                  1653

GCCAGTTAAA  GGCGATTAAT  TCTGCTTCCA  GATAGTCTCC  ACTGTACATA  AAAGTCACAC                  1713
```

```
TGTGTGCTTG CATTCCTGTA TGGTAGTGGT GACTGTCTCT CACACCACCT TCTCTATCAC     1773

GTCACAGTTT TCTCCTCCTC AGCCTATGTC TGCATTCCCC AGAATTCTCC ACTTGTTCCC     1833

TGGCCCTGCT GCTGGACCCT GCTGTGTCTG GTAGGCAACT GTTTGTTGGT GCTTTTGTAG     1893

GGTTAAGTTA AACTCTGAGA TCTTGGGCAA AATGGCAAGG AGACCCAGGA TTCTTCTCTC     1953

CAAAGGTCAC TCCGATGTTA TTTTTGATTC CTGGGGCAGA AATATGACTC CTTTCCCTAG     2013

CCCAAGCCAG CCAAGAGCTC TCATTCTTAG AAGAAAGGC AGCCCCTTGG TGCCTGTCCT      2073

CCTGCCTCGG CTGATTTGCA GAGTACTTCT TCAAAAAGAA AAAAATGGTA AAGCTATTTA     2133

TTAAAAATTC TTTGTTTTTT GCTACAAATG ATGCATATAT TTTCACCCAC ACCAAGCACT     2193

TTGTTTCTAA TATCTTTGAT AAGAAAACTA CATGTGCAGT ATTTATTAA AGCAACATTT      2253

TATTTA                                                                2259
```

(2) INFORMATION FOR SEQ ID NO:36:

(i) SEQUENCE CHARACTERISTICS:
        (A) LENGTH: 357 amino acids
        (B) TYPE: amino acid
        (D) TOPOLOGY: linear (ii) MOLECULE TYPE: protein (xi) SEQUENCE DESCRIPTION: SEQ ID NO:36:

```
Met Glu Glu Gly Met Asn Ile Leu His Asp Phe Gly Ile Gln Ser Thr
  1               5                  10                  15

Arg Tyr Leu Gln Val Asn Tyr Gln Asp Ser Gln Asp Trp Phe Ile Leu
             20                  25                  30

Val Ser Val Ile Ala Asp Leu Arg Asn Ala Phe Tyr Val Leu Phe Pro
         35                  40                  45

Ile Trp Phe His Leu Lys Glu Thr Val Gly Ile Asn Leu Leu Trp Val
     50                  55                  60

Ala Val Val Gly Asp Trp Phe Asn Leu Val Phe Lys Trp Ile Leu Phe
 65                  70                  75                  80

Gly Gln Arg Pro Tyr Trp Trp Val Leu Asp Thr Asp Tyr Tyr Ser Asn
                 85                  90                  95

Ser Ser Val Pro Ile Ile Lys Gln Phe Pro Val Thr Cys Glu Thr Gly
            100                 105                 110

Pro Gly Ser Pro Ser Gly His Ala Met Gly Ala Ala Gly Val Tyr Tyr
        115                 120                 125

Val Met Val Thr Ser Thr Leu Ala Ile Phe Arg Gly Lys Lys Lys Pro
    130                 135                 140

Thr Tyr Gly Phe Arg Cys Leu Asn Val Ile Leu Trp Leu Gly Phe Trp
145                 150                 155                 160

Ala Val Gln Leu Asn Val Cys Leu Ser Arg Ile Tyr Leu Ala Ala His
                165                 170                 175

Phe Pro His Gln Val Val Ala Gly Val Leu Ser Gly Ile Ala Val Ala
            180                 185                 190

Glu Thr Phe Ser His Ile Arg Gly Ile Tyr Asn Ala Ser Leu Arg Lys
        195                 200                 205

Tyr Cys Leu Ile Thr Ile Phe Leu Phe Gly Phe Ala Leu Gly Phe Tyr
    210                 215                 220

Leu Leu Leu Lys Gly Leu Gly Val Asp Leu Leu Trp Thr Leu Glu Lys
225                 230                 235                 240

Ala Lys Arg Trp Cys Glu Arg Pro Glu Trp Val His Leu Asp Thr Thr
```

|     |     |     | 245 |     |     |     |     | 250 |     |     |     |     | 255 |     |
|-----|-----|-----|-----|-----|-----|-----|-----|-----|-----|-----|-----|-----|-----|-----|
| Pro | Phe | Ala | Ser | Leu | Phe | Lys | Asn | Leu | Gly | Thr | Leu | Leu | Gly | Leu | Gly |
|     |     |     | 260 |     |     |     |     | 265 |     |     |     |     | 270 |     |
| Leu | Ala | Leu | Asn | Ser | Ser | Met | Tyr | Arg | Lys | Ser | Cys | Lys | Gly | Glu | Leu |
|     |     | 275 |     |     |     |     | 280 |     |     |     |     | 285 |     |     |
| Ser | Lys | Ser | Phe | Pro | Phe | Arg | Phe | Ala | Cys | Ile | Val | Ala | Ser | Leu | Val |
|     | 290 |     |     |     |     | 295 |     |     |     |     | 300 |     |     |     |
| Leu | Leu | His | Leu | Phe | Asp | Ser | Leu | Lys | Pro | Pro | Ser | Gln | Val | Glu | Leu |
| 305 |     |     |     |     | 310 |     |     |     |     | 315 |     |     |     |     | 320 |
| Ile | Phe | Tyr | Ile | Leu | Ser | Phe | Cys | Lys | Ser | Ala | Thr | Val | Pro | Phe | Ala |
|     |     |     |     | 325 |     |     |     |     | 330 |     |     |     |     | 335 |     |
| Ser | Val | Ser | Leu | Ile | Pro | Tyr | Cys | Leu | Ala | Arg | Ile | Leu | Gly | Gln | Thr |
|     |     |     | 340 |     |     |     |     | 345 |     |     |     |     | 350 |     |
| His | Lys | Lys | Ser | Leu |
|     |     | 355 |     |     |

THE CATALYTIC MOIETY OF THE GLUCOSE-6-PHOSPHATASE SYSTEM: THE GENE AND PROTEIN AND RELATED MUTATIONS

BACKGROUND OF THE INVENTION

The present invention relates to nucleic acid sequences and methods useful for producing recombinant glucose-6-phosphatase (G-6-Pase). In addition, the present invention relates to specific mutations in the gene encoding human G-6-Pase and methods for detecting the mutations and thus diagnosing the genetic disease that causes glycogen storage disease type 1A.

Glucose-6-phosphatase catalyzes the terminal reaction in gluconeogenesis and glycogenolysis and is integral to the endoplasmic and nuclear membrane. The enzyme is thought to be arranged in the native microsomal membrane in such a way that it is not directly accessible to its substrate as well as inhibitors of low molecular mass nor to antibodies or proteases from the cytoplasmic surface. The enzyme may traverse the microsomal membrane as an integral channel protein. The catalytic region of G-6-Pase is theorized as being part of a channel which is maintained by the native conformation of the enzyme that in turn is elicited by the intimate microenvironment of the membrane. With this in mind, the specificity for glucose-6-phosphatase, development of latency, the high thermal sensitivity induced by detergent treatment of the native membrane, and the kinetic response to chemical modifying agents are considered to be properties of the enzyme itself, and not secondary reactions resulting from membrane disruption.

The solubilization of the enzyme from its natural lipid environment leads to rapid and irreversible inactivation and as a result has hindered purification. The purification of a detergent-soluble pyridoxylated G-6-Pase from rat liver was reported by Speth, M. and H.-U. Schulze in *Eur. J. Biolchem.*, 208:643–650 (1992), incorporated herein by reference. The 700-fold purification was achieved by covalently labeling of the enzyme in native rat liver microsomes with pyridoxal 5'-phosphate and $NaBH_4$, followed by solubilization of the microsomes with Triton X-100, chromatography on phenyl-Sepharose, hydroxyapatite, DEAE-Sephacel and a second chromatography step on hydroxyapatite. Analysis of the purified enzyme on SDS/PAGE showed a band migrating at 35-kDa. Purification was achieved due to the interaction between the negatively charged enzyme-bound phosphate label of the pyridoxylated G-6-Pase and the $Ca^+$ of the hydroxyapatite resin.

Glycogen metabolism in the liver plays a major role in the homeostatic regulation of blood glucose levels. The synthesis and degradation of glycogen are tightly regulated by homeostatic and hormonal mechanisms which ensure an optimal utilization of the polysaccharide.

Glycogen storage diseases are known to be the result of at least 10 different genetic defects within the group of enzymes and transport proteins required by glycogen metabolism. Glycogen storage disease Type Ia (GSD, also known as yon Gierke disease) is defined as the deficiency of glucose-6-phosphatase which is normally present in liver, kidney, and intestine. In a subgroup of the disease, types 1b, 1c and 1d, the putative cause is the deficiency of three transport proteins termed T1, T2 and T3, respectively. These transport proteins allow the substrates and products, glucose-6-phosphate, phosphate (and pyrophosphate) and glucose to cross the endoplasmic reticulum membrane. Glycogen storage disease type 1a is inherited by 1 in 100,000 to 300,000 as an autosomal recessive trait and is usually manifested during the first 12 months of life by symptomatic hypoglycemia, or by the recognition of hepatomegaly. In addition, GSD type 1a can have indications of growth retardation, delayed adolescence, lacticacidemia, hyperlipidemia, hyperuricemia, and in adults, hepatic adenomas.

While it is known that GSD type 1a is due to inactive G-6-Pase and the cause of this inactivity most likely genetic, the specific genetic alterations are unknown. Knowledge of the gene sequence encoding G-6-Pase as well as the mutated gene sequences that result in inactive G-6-Pase is an important and basic discovery toward understanding the molecular basis of this disorder and for developing diagnostic tools and therapeutic treatments. To these ends the present invention disclosing the gene sequence of human as well as murine G-6-Pase (Seq. ID No.:35) and mutations that result in inactive human G-6-Pase is presented.

SUMMARY OF THE INVENTION

This invention provides for nucleic acid sequences that are capable of selectively hybridizing to genomic nucleic acid sequences of glucose-6-phosphosphatase. The nucleic acid selectively hybridizes to the nucleic acid of Seq. ID No. 1 or to intron sequences of the genomic nucleic acid. The hybridization occurs under hybridization wash conditions consisting of 0.2 X SSC, 0.1% SDS, and 65° C.

The nucleic acid may be all of Seq. ID No.1 or a partial sequence from Seq. ID No.1. The nucleic acid may have changes in Seq. ID No. 1 that are due to mutations. Such mutations are: an insertion of TA at nucleotide position 459 of Seq. ID No. 1, C is replaced with a T at nucleotide position 326 of Seq. ID No. 1, C is replaced with T at nucleotide position 962 of Seq. ID No. 1, or C is replaced with a T at nucleotide position 1118 of Seq. ID No. 1. In addition, the nucleotide sequence may be from nucleotide sequences from the introns of the genomic sequence of G-6-Pase.

The invention further provides for G-6-Pase proteins (Seq. ID No.:2) that are encoded by Seq. ID No. 1 and mutated G-6-Pase proteins encoded by changes to nucleotide positions within Seq. ID No. 1. Such mutated proteins are: a truncated G-6-Pase of 129 amino acids due to the insertion of TA at nucleotide position 459, (Seq. ID No.:3) a mutated G-6-Pase having Arg replaced with a Cys at amino acid position 83 (Seq. ID No.:4), a mutated G-6-Pase having Arg changed to Cys at amino acid position 295 (Seq. ID No.: 6), a truncated G-6-Pase of 346 amino acids due to a C to T mutation at nucleotide 1118 of Seq. ID No. 1 that converts a glutamine to a stop codon at amino acid position 347 (Seq. ID No.: 5).

In addition, the invention provides for recombinant vectors that contain nucleic acid sequences that encode sequences of G-6-Pase and mutated G-6-Pase. The sequences can be operably linked to a promoter and be expressed in either prokaryotic and eukaryotic hosts.

In a further embodiment, the invention provides for methods of detecting in a test sample the presence or absence of mutation in a nucleotide sequence essentially encoding human G-6-Pase. The method comprises contacting the test sample with a first nucleic acid sequence having a sequence competent to discriminate between the wild type gene and the mutant gene and then detecting the formation of a duplex between the gene and the first nucleotide sequence. The first nucleotide sequence will selectively hybridize to mutant sequences of G-6-Pase. The first nucleic acid may be a polymerase chain reaction primer which binds to an intron of the human G-6-Pase gene. The first nucleic acid may be a PCR primer which discriminates between wild-type and mutant forms of the human G-6-Pase gene using allelic specific polymerase chain reaction. The first nucleic acid may bind to exons or introns of the genomic DNA of the G-6-Pase gene.

A further embodiment of the invention are kits for detecting wild-type or mutant G-6-Pase genes comprising; a) a container holding a first nucleotide sequence capable of discrimination between wild-type and mutant forms of the gene; and b) a container holding a reagent for detecting the formation of a duplex between the gene and the first nucleotide sequence. The first nucleotide sequence of the kit can be a PCR primer pair which amplify a region of the G-6-Pase gene containing a mutation. The primer pair can specifically bind to the human genomic DNA sequence containing the G-6-Pase gene.

BRIEF DESCRIPTION OF THE DRAWINGS

FIG. 2 shows nucleotide and corresponding protein for the catalytic moiety of the human glucose-6-phosphatase system.

DEFINITIONS

Figure 1:
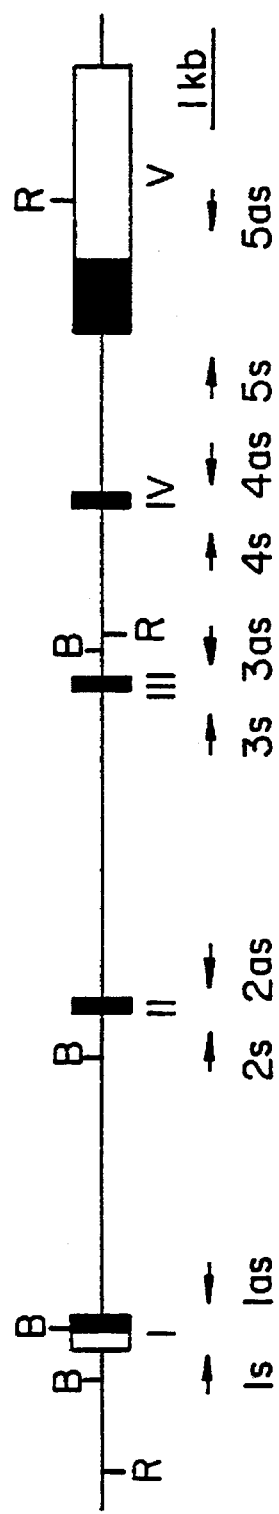
FIG. 1 shows the structural organization of the human G-6-Pase genomic transcription unit. The exon coding regions are indicated by filled boxes and the untranslated regions, open boxes. Arrows indicate oligonucleotide primer pairs used for amplification of exons. Restriction enzyme sites are indicated by: B for Bam HI and R for Eco RI.

"Amplification" primers are oligonucleotides comprising either natural or analog nucleotides that can serve as the basis for the amplification of a select nucleic acid sequence. They include both polymerase chain reaction primers and ligase chain reaction oligonucleotides.

"Nucleic acids", as used herein, may be DNA or RNA Additionally, substantial nucleic acid sequence identity exists when a nucleic acid segment will hybridize, under stringent hybridization conditions, to a complement of another nucleic acid strand.

The phrase "nucleotide sequence" includes both the sense and antisense strands as either individual single strands or in the duplex.

The phrase "DNA sequence" refers to a single or double stranded DNA molecule composed of the nucleotide bases, adenosine, thymidine, cytosine and guanosine.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences includes both the full length nucleic acid sequences as well as non-full length sequences derived from the full length sequences. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

"Isolated" or "substantially pure" when referring to nucleic acid sequences encoding the G-6-Pase protein or fragments thereof refers to isolated nucleic acids which do not encode proteins or peptides other than G-6-Pase protein or peptides.

The term "recombinant" refers to DNA which has been isolated from its native or endogenous source and modified either chemically or enzymatically to delete naturally-occurring flanking nucleotides or provide flanking nucleotides that do not naturally occur. Flanking nucleotides are those nucleotides which are either upstream or downstream from the described sequence or sub-sequence of nucleotides.

The term "vector" refers to viral expression systems, autonomous self-replicating circular DNA (plasmids), and includes both the expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The phrase "selectively hybridizing to or specifically hybridizing to", refers to a nucleic acid that hybridizes duplexes or binds only to DNA sequences encoding one protein or portions thereof when the DNA sequences encoding the protein are present in a cDNA library. A DNA sequence which selectively hybridizes to a given target sequence can include sequences which are shorter or longer than the target sequence so long as they meet the functional test set forth. Hybridization conditions are specified along with the source of the cDNA library. Typically the hybridization is done in a Southern blot protocol using a 0.2XSSC, 0.1% SDS, 65° C. wash as described in examples 1 and 2 herein.

The term "competent to discriminate between the wild type gene and the mutant form" means a hybridization probe or primer sequence that allows the trained artisan to detect the presence or absence of base changes or additions to the nucleotide sequence encoding G-6-Pase. A probe sequence will be a sequence containing the site that is changed or added to. A primer sequence will hybridize with the sequences surrounding the base changes or additions and using the gene sequence as template allow the further synthesis of nucleotide sequences that contain the base changes or additions. In addition, the probe may act as a primer. It is important to point out that this invention allows for the design of PCR primers capable to amplify entire exons. To achieve this, primers need hybridize with intron sequences. This invention provides such intron sequences.

The term "SSC" refers to a citrate-saline solution of 0.15 M sodium chloride and 20 mM sodium citrate. Solutions are often expressed as multiples or fractions of this concentration. For example, 6XSSC refers to a solution having a sodium chloride and sodium citrate concentration of 6 times this amount or 0.9 M sodium chloride and 120 mM sodium citrate. 0.2XSSC refers to a solution 0.2 times the SSC concentration or 0.03 M sodium chloride and 4 mM sodium citrate.

The term "plasmid" refers to an autonomous self-replicating circular DNA molecule and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

"Biological sample" refers to any sample obtained from a living organism or from an organism that has died. Examples of biological samples include body fluids and tissue specimens. In the case of microorganisms a biological sample may include samples containing many entire organisms.

The phrase "biologically pure" refers to material which is substantially or essentially free from components which normally accompany it as found in its native state. Thus, the G-6-Pase molecules of this invention do not contain materials normally associated with their in situ environment, e.g., other cytosolic or peroxisomal proteins. Even where a protein has been isolated to a homogenous or dominant band using standard electrophoretic techniques, there are trace contaminants in the range of 5–10% of native protein which co-purify with the desired protein. Biologically pure material does not contain such endogenous co-purified protein.

The phrase "genomic" refers to DNA which includes both the exon and intron regions as well as the untranslated sequences that are 5' exon 1 and 3' of exon 5 of the G-6-Pase gene. Intron 1 is between exon I and exon II, intron 2 is between exon II and exon III, intron 3 is between exon III and exon IV, and intron 4 is between exon IV and exon V.

DETAILED DESCRIPTION

This invention provides for the expression and genomic analysis of the G-6-Pase gene. Genomic analysis will provide particularly useful information regarding persons suspected of carrying or having glycogen storage disease type 1A. The cDNA encoding the G-6-Pase gene is provided along with select introns from the human gene. The entire human gene has not been sequenced. It is approximately 12 Kb in length. A map of the gene with both the introns and exons identified is provided in FIG. 1. Using the map and the sequences provided herein, one of skill following the outlined procedures could readily identify alternative intron sequences which could be used to identify the mutants described herein.

A. General Recombinant DNA Methods.

This invention relies on routine techniques in the field of recombinant genetics. A basic text disclosing the general methods of use in this invention is Sambrook et al., *Molecular Cloning, A Laboratory Manual*, Cold Spring Harbor Publish., Cold Spring Harbor, N.Y. 2nd ed. (1989) and Kriegler, *Gene Transfer and Expression: A Laboratory Manual*, W.H. Freeman, N.Y., (1990), which are both incorporated herein by reference. Unless otherwise stated all enzymes are used in accordance with the manufacturer's instructions.

Nucleotide sizes are given in either kilobases (Kb) or base pairs (bp). These are estimates derived from agarose or acrylamide gel electrophoresis or from published DNA sequences.

Oligonucleotides that are not commercially available can be chemically synthesized according to the solid phase phosphoramidite triester method first described by S.L. Beaucage and M.H. Caruthers, *Tetrahedron Letts.*, 22(20):1859–1862 (1981), using an automated synthesizer, as described in D.R. Needham Van Devanter et. al., *Nucleic Acids Res.*, 12:6159–6168, 1984. Purification of oligonucleotides is by either native acrylamide gel electrophoresis or by anion-exchange HPLC as described in J.D. Pearson and F.E. Reanier, *J. Chrom.*, 255:137–149, 1983.

The sequence of the cloned genes and synthetic oligonucleotides can be verified using the chemical degradation method of A.M. Maxam et al., *Methods in Enzymology*, 65:499560, (1980). The sequence can be confirmed after the assembly of the oligonucleotide fragments into the double-stranded DNA sequence using the method of Maxam and Gilbert, supra, or the chain termination method for sequencing double-stranded templates of R.B. Wallace et al. Gene, 16:21–26, 1981. Southern Blot hybridization techniques are carried out according to Southern et al., *J. Mol. Biol.*, 98:503, 1975.

B. Cloning Methods for the Isolation of Nucleotide Sequences Encoding Glucose-6-Phosphatase Proteins.

In general, the nucleic acid sequences encoding G-6-Pase are cloned from DNA sequence libraries that are made to encode copy DNA (cDNA) or genomic DNA. The particular sequences can be located by hybridizing with an oligonucleotide probe, the sequence of which can be derived from Seq. I.D. Nos.: 1 or 35. The desired target sequences may also be obtained using polymerase chain reaction (PCR) primers which amplify either the entire gene, cDNA or portions there of. PCR primers can be selected from the sequences provided herein. Alternatively, where the sequence is cloned into an expression library, the expressed recombinant G-6-Pase can be detected immunologically with antisera or purified antibodies made against G-6-Pase.

To make the cDNA library, one should choose a source that is rich in mRNA. For example, liver is enriched for mRNA of glucose-6-phosphatase. The mRNA can then be made into cDNA, ligated into a recombinant vector, and transfected into a recombinant host for propagation, screening and cloning. Methods for making and screening cDNA libraries are well known. See Gubler, U. and Hoffman, B.J. *Gene* 25:263–269, 1983 and Sambrook.

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro, as described in Sambrook. Recombinant phage are analyzed by plaque hybridization as described in Benton and Davis, *Science*, 196:180–182 (1977). Colony hybridization is carried out as generally described in M. Grunstein et al. *Proc. Natl. Acad. Sci. USA.*, 72:3961–3965 (1975).

An alternative method combines the use of synthetic oligonucleotide primers with polymerase extension on an mRNA or DNA template. This polymerase chain reaction (PCR) method amplifies nucleic acid sequences of the G-6-Pase gene directly from mRNA, from cDNA, from genomic libraries or cDNA libraries. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of G-6-Pase mRNA in physiological samples, for nucleic acid sequencing, or for other purposes. U.S. Pat. Nos. 4,683,195 and 4,683,202 describe this method. Genes amplified by the PCR reaction can be purified from agarose gels and cloned into an appropriate vector.

Appropriate primers and probes for identifying G-6-Pase protein from alternative mammalian tissues are generated from comparisons of the sequences provided herein. For a general overview of PCR see *PCR Protocols: A Guide to Methods and Applications.* (Innis, M, Gelfand, D., Sninsky, J. and White, T., eds.), *Academic Press,* San Diego (1990), incorporated herein by reference.

Synthetic oligonucleotides can be used to construct genes. This is done using a series of overlapping oligonucleotides usually 40–120 bp in length, representing both the sense and nonsense strands of the gene. These DNA fragments are then annealed, ligated and cloned.

The gene for G-6-Pase is cloned using intermediate vectors before transformation into mammalian cells for expression. These intermediate vectors are typically prokaryote vectors or shuttle vectors. The G-6-Pase protein can be expressed in either prokaryotes or eukaryotes.

In summary, the G-6-Pase gene can prepared by probing or amplifying select regions of a mixed cDNA or genomic pool using the probes and primers generated from the sequences provided herein.

C. Expression in Prokaryotes

To obtain high level expression of a cloned gene, such as those cDNAs encoding G-6-Pase in a prokaryotic system, it is essential to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.,* 158:1018–1024 (1984), and the leftward promoter of phage lambda ($P_L$) as described by Herskowitz,I. and Hagen, D., *Ann. Rev. Genet.,* 14:399–445 (1980).

Expression systems for expressing the G-6-Pase protein are available using *E. coli, Bacillus sp.* and Salmonella (Palva, Iet al., *Gene* 22:229–235 (1983); Mosbach, K. et al., *Nature,* 302:543–545 (1983).

The G-6-Pase protein produced by prokaryote cells will not be glycosylated and may not necessarily fold properly. During purification from *E. coli*, the expressed G-6-Pase protein may first be denatured and then renatured. This can be accomplished by solubilizing the bacterially produced proteins in a chaotropic agent such as guanidine HCl and reducing all the cysteine residues with a reducing agent such as beta- mercaptoethanol. The protein is then renatured, either by slow dialysis or by gel filtration. U.S. Pat. No.4, 511,503.

When expressing G-6-Pase protein in *S. typhimurium*, one should be aware of the inherent instability of plasmid vectors. To circumvent this, the foreign gene can be incorporated into a nonessential region of the host chromosome. This is achieved by first inserting the gene into a plasmid such that it is flanked by regions of DNA homologous to the insertion site in the Salmonella chromosome. After introduction of the plasmid into the *S. typhimurium*, the foreign gene is incorporated into the chromosome by homologous recombination between the flanking sequences and chromosomal DNA.

An example of how this could be achieved is based on the his operon of Salmonella. Two steps are involved in this process. Firstly, a segment of the his operon must be deleted in the Salmonella strain selected as the carrier. Secondly, a plasmid carrying the deleted his region downstream of the gene encoding the G-6-Pase protein is transformed into the his Salmonella strain. Integration of both the his sequences and the gene encoding the G-6-Pase protein occurs, resulting in recombinant strains which can be selected as his$^+$.

Detection of the expressed protein is achieved by methods known in the art as radioimmunoassays, or Western blotting techniques or immunoprecipitation. Purification from *E. coli* can be achieved following procedures described in U.S. Pat. No. 4,511,503.

D. Expression in Eukaryotes

Standard eukaryotic transfection methods are used to produce mammalian, yeast or insect cell lines which express large quantities of G-6-Pase protein which are then purified using standard techniques. See, e.g., Colley et al., *J. Biol. Chem.* 264:17619–17622, (1989), and Guide to Protein Purification, in Vol. 182 of *Methods in Enzymology* (Deutscher ed., 1990), both of which are incorporated herein by reference.

Transformations of eukaryotic cells are performed according to standard techniques as described by D.A. Morrison, *J. Bact.,* 132:349–351 (1977), or by J.E. Clark-Curtiss and R. Curtiss, *Methods in Enzymology,* 101:347–362, Eds. R. Wu et. al., Academic Press, New York (1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see Sambrook et al., supra). It is only necessary that the particular genetic engineering procedure utilized be capable of successfully introducing at least one gene into the host cell which is capable of expressing the G-6-Pase protein.

The particular eukaryotic expression vector used to transport the genetic information into the cell is not particularly critical. Any of the conventional vectors used for expression in eukaryotic cells may be used. Expression vectors containing regulatory elements from eukaryotic viruses are typically used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/$A^+$, pMTO10/$A^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

The vectors usually comprise selectable markers which result in gene amplification such as the sodium, potassium ATPase, thymidine kinase, aminoglycoside phosphotransferase, hygromycin B phosphotransferase, xanthine-guanine phosphoribosyl transferase, CAD (carbamyl phosphate synthetase, aspartate transcarbamylase, and dihydroorotase), adenosine deaminase, dihydrofolate reductase, and asparagine synthetase and ouabain selection. Alternatively, high yield expression systems not involving gene amplification are also suitable, such as using a bacculovirus vector in insect cells, with the G-6-Pase encoding sequence under the direction of the polyhedrin promoter or other strong baculovirus promoters.

The expression vector of the present invention will typically contain both prokaryotic sequences that facilitate the cloning of the vector in bacteria as well as one or more eukaryotic transcription units that are expressed only in eukaryotic cells, such as mammalian cells. The vector may or may not comprise a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the transfected DNA integrates into the genome of the transfected cell, where the promoter directs expression of the desired gene. The expression vector is typically constructed from elements derived from different, well characterized viral or mammalian genes. For a general discussion of the expression of cloned genes in cultured mammalian cells, see Sambrook et al., supra, Ch. 16.

The prokaryotic elements that are typically included in the mammalian expression vector include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells.

The expression vector contains a eukaryotic transcription unit or expression cassette that contains all the elements required for the expression of the G-6-Pase DNA in eukaryotic cells. A typical expression cassette contains a promoter operably linked to the DNA sequence encoding a G-6-Pase protein and signals required for efficient polyadenylation of the transcript. The DNA sequence encoding the G-6-Pase protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of Heliothis virescens. Additional elements of the cassette may include enhancers and, if genomic DNA is used as the structural gene, introns with functional splice donor and acceptor sites.

Eukaryotic promoters typically contain two types of recognition sequences, the TATA box and upstream promoter elements. The TATA box, located 25–30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus, the long term repeat from various retroviruses such as murine leukemia virus, murine or Rous sarcoma virus and HIV. See, Enhancers and Eukaryotic Expression, Cold Spring Harbor Pres, Cold Spring Harbor, N.Y. 1983, which is incorporated herein by reference.

In the construction of the expression cassette, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently translated, polyadenylation sequences are also commonly added to the vector construct. Two distinct sequence elements are required for accurate and efficient polyadenylation: GU or U rich sequences located downstream from the polyadenylation site and a highly conserved sequence of six nucleotides, AAUAAA, located 11–30 nucleotides upstream. Termination and polyadenylation signals that are suitable for the present invention include those derived from SV40, or a partial genomic copy of a gene already resident on the expression vector.

In addition to the elements already described, the expression vector of the present invention may typically contain other specialized elements intended to increase the level of expression of cloned genes or to facilitate the identification of cells that carry the transfected DNA. For instance, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

After the expression vector is introduced into the cells, the transfected cells are cultured under conditions favoring expression of the G-6-Pase protein which is recovered from the culture using standard techniques 1. Expression in Yeast Synthesis of heterologous proteins in yeast is well known and described. Methods in Yeast Genetics, Sherman, F., et al., Cold Spring Harbor Laboratory, (1982) is a well recognized work describing the various methods available to produce G-6-Pase protein in yeast.

For high level expression of a gene in yeast, it is essential to connect the gene to a strong promoter system as in the prokaryote and also to provide efficient transcription termination/polyadenylation sequences from a yeast gene. Examples of useful promoters include GAL1,10 (Johnson, M., and Davies, R.W., Mol. and Cell. Biol., 4:1440–1448 (1984)) ADH2 (Russell, D., et al., J. Biol. Chem., 258:2674–2682, (1983)), PHO5 (EMBO J. 6:675–680, (1982)), and MFα1. A multicopy plasmid with a selective marker such as Leu-2, URA-3, Trp-1, and His-3 is also desirable.

The MFα1 promoter is preferred. The MFα1 promoter, in a host of the α mating-type is constitutive, but is switched off in diploids or cells with the a mating-type. It can, however, be regulated by raising or lowering the temperature in hosts which have a ts mutation at one of the SIR loci. The effect of such a mutation at 35° C. on an α type cell is to turn on the normally silent gene coding for the α mating-type. The expression of the silent a mating-type gene, in turn, turns off the MFα1 promoter. Lowering the temperature of growth to 27° C. reverses the whole process, i.e., turns the a mating-type off and turns the MFα1 on (Herskowitz, I. and Oshima, Y., in The Molecular Biology of the Yeast Saccharomyces, (eds. Strathern, J.N. Jones, E.W., and Broach, J.R., Cold Spring Harbor Lab., Cold Spring Harbor, N.Y., pp.181–209, (1982).

The polyadenylation sequences are provided by the 3'-end sequences of any of the highly expressed genes, like ADH1, MFα1, or TPI (Alber, T. and Kawasaki, G., J. of Mol. & Appl. Genet. 1:419–434, (1982).

A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17–24, (1979); Broach, et al., Gene, 8:121–133, (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J.D. Beggs, Nature (London), 275:104–109, (1978); and Hinnen, A., et al., Proc. Natl. Acad. Sci. USA, 75:1929–1933, (1978). The second procedure does not involve removal of the cell wall. Instead the cells are treated with lithium chloride or acetate and PEG and put on selective plates (Ito, H., et al., J. Bact., 153:163–168, (1983)).

Glucose-6-phosphatase protein can be isolated from yeast by lysing the cells and applying standard protein isolation techniques to the lysates. The monitoring of the purification process can be accomplished by using Western blot techniques or radioimmunoassays.

2. Expression in insect cells

The baculovirus expression vector utilizes the highly expressed and regulated Autographa californica nuclear polyhedrosis virus (AcMNPV) polyhedrin promoter modified for the insertion of foreign genes. Synthesis of polyhedrin protein results in the formation of occlusion bodies in the infected insect cell. The recombinant proteins expressed using this vector have been found in many cases to be, antigenically, immunogenically, and functionally similar to their natural counterparts. In addition, the baculovirus vector utilizes many of the protein modification, processing, and transport systems that occur in higher eukaryotic cells.

Briefly, the DNA sequence encoding G-6-Pase is inserted into a transfer plasmid vector in the proper orientation downstream from the polyhedrin promoter, and flanked on both ends with baculovirus sequences. Cultured insect cell, commonly Spodoptera frugiperda, are transfected with a mixture of viral and plasmid DNAs. The virus that develop, some of which are recombinant virus that result from homologous recombination between the two DNAs, are plated at 100–1000 plaques per plate. The plaques containing recombinant virus can be identified visually because of their ability to form occlusion bodies or by DNA hybridization. The recombinant virus is isolated by plague purification. The resulting recombinant virus, capable of expressing G-6-Pase, is self propagating in that no helper virus is required for maintenance or replication. After infecting an insect culture with recombinant virus, one can expect to find recombinant protein within 48–72 hours. The infection is essentially lytic within 4–5 days.

There are a variety of transfer vectors into which the G-6-Pase gene can be inserted. For a summary of transfer vectors see Luckow, V.A. and M.D. Summers, Bio/Technology, 6:47–55 (1988). Preferred is the transfer vector pAcUW21 described by Bishop, D.H.L. in Seminars in Virology, 3:253–164, (1992).

3. Expression in recombinant vaccinia virus-infected cells

The gene encoding G-6-Pase protein is inserted into a plasmid designed for producing recombinant vaccinia, such as pGS62, Langford, C.L., et al., Mol. Cell. Biol. 6:3191–3199, (1986). This plasmid consists of a cloning site for insertion of foreign genes, the P7.5 promoter of vaccinia to direct synthesis of the inserted gene, and the vaccinia TK gene flanking both ends of the foreign gene.

When the plasmid containing the G-6-Pase gene is constructed, the gene can be transferred to vaccinia virus by homologous recombination in the infected cell. To achieve this, suitable recipient cells are transfected with the recombinant plasmid by standard calcium phosphate precipitation techniques into cells already infected with the desirable strain of vaccinia virus, such as Wyeth, Lister, WR or Copenhagen. Homologous recombination occurs between the TK gene in the virus and the flanking TK gene sequences in the plasmid. This results in a recombinant virus with the foreign gene inserted into the viral TK gene, thus rendering the TK gene inactive. Cells containing recombinant viruses are selected by adding medium containing 5-bromodeoxyuridine, which is lethal for cells expressing a TK gene.

Confirmation of production of recombinant virus can be achieved by DNA hybridization using cDNA encoding the G-6-Pase protein and by immunodetection techniques using antibodies specific for the expressed protein. Virus stocks may be prepared by infection of cells such as HeLA S3 spinner cells and harvesting of virus progeny.

4. Expression in Cell Cultures

Glucose-6-phosphatase cDNA can be ligated to various expression vectors for use in transforming host cell cultures. The vectors typically contain gene sequences to initiate transcription and translation of the G-6-Pase gene. These sequences need to be compatible with the selected host cell. In addition, the vectors preferably contain a marker to provide a phenotypic trait for selection of transformed host cells such as dihydrofolate reductase or metallothionein. Additionally, a vector might contain a replicative origin.

Cells of mammalian origin are illustrative of cell cultures useful for the production of the G-6-Pase. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

As indicated above, the vector, e.g., a plasmid, which is used to transform the host cell, preferably contains DNA sequences to initiate transcription and sequences to control the translation of the G-6-Pase gene sequence. These sequences are referred to as expression control sequences. Illustrative expression control sequences are obtained from the SV-40 promoter (Science, 222:524–527, (1983)), the CMV I.E. Promoter (Proc. Natl. Acad. Sci. 81:659–663, (1984)) or the metallothionein promoter (Nature 296:39–42, (1982)). The cloning vector containing the expression control sequences is cleaved using restriction enzymes and adjusted in size as necessary or desirable and ligated with sequences encoding the G-6-Pase protein by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., J. Virol. 45: 773–781, (1983)).

Additionally gene sequences to control replication in the host cell may be incorporated into the vector such as those found in bovine papilloma virus type-vectors. Saveria-Campo, M., "Bovine Papilloma virus DNA a Eukaryotic Cloning Vector" in DNA Cloning Vol. II a Practical Approach Ed. D.M. Glover, IRL Press, Arlington, Va. pp. 213–238, (985).

The transformed cells are cultured by means well known in the art. For example, as published in Biochemical Methods in Cell Culture and Virology, Kuchler, R.J., Dowden, Hutchinson and Ross, Inc., (1977). The expressed G-6-Pase protein is isolated from cells grown as suspensions or as monolayers. The latter are recovered by well known mechanical, chemical or enzymatic means.

E. Protein Purification

Purification of G-6-Pase is obtained using a combination of protein purification steps known in the art. As described supra, G-6-Pase is integrally associated with the endoplasmic reticulum. As a result, subcellular fractionation of the recombinant cells causes the formation of endoplasmic reticulum vesicles called microsomes. As an initial step in the purification, microsomes are prepared by differential centrifugation as described by Carter, B.R., et al., Biochem. J., 148:279–294 (1975), incorporated herein by reference. The intact nature of the microsomes can be determined on the basis of low $K_m$ mannose-6-phosphatase activity as described by Arion, W., et al., J. Biol. Chem., 251:4901–4907 (1976) incorporated herein by reference. Expressed G-6-Pase is isolated from the microsomal fraction by the methods described by Speth, M. and H.-U. Schulze, supra, incorporated herein by reference. Briefly, the enzyme is first covalently labeled with pyridoxal 5'-phosphate and $NaBH_4$ while still associated with the microsomal fraction. Next, the microsome fraction is disrupted with Triton X-100, chromatographed over phenyl-Sepharose, hydroxyapatite, DEAE-Sephacel. The final purification step is a chromatographic separation over hydroxyapatite. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon staining.

F. Enzyme Assay

Phosphohydrolase activity can be determined essentially as described by Burchell et al. Clin. Chim. Acta 173, 183–192 (1988). Reaction mixtures (100 μl) contain 50 mM cacodylate buffer, pH 6.5, 10 mM glucose-6-P (or mannose-6-P), 2 mM EDTA, and appropriate amounts of microsomal proteins. After incubation at 30° C. for 10 min, reactions are stopped by the addition of 4 volumes of a solution containing 2.1 mM ammonium molybdate, 0.33 M sulfuric acid, 3.3% SDS, and 0.07 M ascorbic acid. Sample absorbance is then determined at 820 nm and is related to the amount of phosphate released using a standard curve constructed by a stock of inorganic phosphate solution. In addition, one can use a radioassay for determination of glucose release from glucose-6-phosphate following the method of Bublitz, C., Mol. Cell. Biochem., 108:141–144, (1991). Briefly, the reaction mixture (400 μl) contains 50 mM cacodylate buffer, pH 6.5, 8 mM glucose-6-P, $^{14}$C-glucose-6-P, and appropriate amounts of microsomal proteins of purified G-6-Pase.

After incubation at 30C for 10 min., reactions are stopped by the addition of 2 volumes of a slurry of Dowex 2 fluoride in ethanol. The reaction mixtures are shaken for 1 min. in order to absorb the glucose-6-P. $^{14}$C-glucose released in supernatant fraction is then determined after centrifugation.

In addition, glucose-6-phosphatase can be assayed by determination of glucose released from glucose-6-phosphate using the coupled glucose oxidase/peroxidase enzyme system as described by Bergmeyer, H.-U. and E. Bernt in Methoden der enzymatischem Analyse (Bergmeyer, H.-U., ed) pp.1172–1181, Verlag Chemie, Weinheim, incorporated herein by reference.

G. Latency of Glucose-6-Phosphatase

When G-6-Pase activity is assayed in microsomal samples in the test tube, the enzyme is more active in disrupted microsomal vesicles than in intact microsomes. When enzyme activity increases after microsome disruption, the enzyme is exhibiting latency. This is because the active site of the enzyme is located inside the lumen of the endoplasmic reticulum. As a result, the substrates and products of the enzyme have to cross the membrane of the endoplasmic reticulum.

G. Measurement of the G-6-Pase Gene and Protein

1. G-6-Pase DNA and RNA Measurement

The present invention also provides methods for detecting the presence or absence of G-6-Pase DNA or RNA in a physiological specimen. The most preferred specimen will be neonatal blood samples where expression of the G-6-Pase gene is minimal. Genomic analysis is preferred and the mutations of this gene will involve using primers and probes which bind to either the exons or introns of the G-6-Pase gene. A map of this gene is provided in FIG. 1.

A variety of methods of specific DNA and RNA measurement using nucleic acid hybridization techniques are known to those of skill in the art. See Sambrook. For example, one method for evaluating the presence or absence of G-6-Pase DNA in a sample involves a Southern transfer. Briefly, the digested genomic DNA is run on agarose slab gels in buffer and transferred to membranes. Hybridization is carried out using the probes discussed above. Visualization of the hybridized portions allows the qualitative determination of the presence or absence of G-6-Pase genes.

Similarly, a Northern transfer may be used for the detection of G-6-Pase mRNA in samples of RNA from cells expressing the G-6-Pase gene. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the G-6-Pase transcript.

The selection of a nucleic acid hybridization format is not critical. A variety of nucleic acid hybridization formats are known to those skilled in the art. For example, common formats include sandwich assays and competition or displacement assays. Hybridization techniques are generally described in "Nucleic Acid Hybridization, A Practical Approach," Ed Hames, B D. and Higgins, S J , IRL Press, 1985; Gall and Pardue (1969), Proc. Natl. Acad. Sci., U.S.A., 63:378–383; and John, Burnsteil and Jones (1969) Nature, 223:582–587.

For example, sandwich assays are commercially useful hybridization assays for detecting or isolating nucleic acid sequences. Such assays utilize a "capture" nucleic acid covalently immobilized to a solid support and labelled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

The nucleic acid sequences used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may act as a negative probe in an assay sample where only the mutant G-6-Pase is present.

Typically labelled signal nucleic acids are used to detect hybridization. Complementary nucleic acids or signal nucleic acids may be labelled by any one of several methods typically used to detect the presence of hybridized polynucleotides. The most common method of detection is the use of autoradiography with $^3H$, $^{125}I$, $^{35}S$, $^{14}C$, or $^{32}P$-labelled probes or the like. Other labels include ligands which bind to labelled antibodies, fluorophores, chemiluminescent agents, enzymes, and antibodies which can serve as specific binding pair members for a labelled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label. (Tijssen, P., "Practice and Theory of Enzyme Immunoassays," Laboratory Techniques in Biochemistry and Molecular Biology, Burdon, R.H., van Knippenberg, P.H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

A preferred embodiment is the use of allelic specific amplifications. In the case of PCR, the amplification primers are designed to bind to a portion of the G-6-Pase gene but the terminal base at the 3' end is used to discriminate between the mutant and wild-type forms of the G-6-Pase gene. If the terminal base matches the point mutation or the wild-type, polymerase dependent three prime extension can proceed and an amplification product is detected. This method for detecting point mutations or polymorphisms is described in detail by Sommer, S.S., et al., in Mayo Clin. Proc. 64:1361–1372,(1989), incorporated herein by reference. By using appropriate controls, one can develop a kit having both positive and negative amplification products. The products can be detected using specific probes or by simply detecting their presence or absence. A variation of the PCR method uses LCR where the point of discrimination, i.e, either the point mutation or the wild-type bases fall between the LCR oligonucleotides. The ligation of the oligonucleotides becomes the means for discriminating between the mutant and wild-type forms of the G-6-Pase gene.

An alternative means for determining the level of expression of the G-6-Pase gene is in situ hybridization. In situ hybridization assays are well known and are generally described in Angerer, et al., Methods Enzymol., 152:649–660 (1987). In an in situ hybridization assay cells, preferentially bovine lymphocytes are fixed to a solid support, typically a glass slide. If DNA is to be probed, the cells are denatured with heat or alkali. The cells are then contacted with a hybridization solution at a moderate temperature to permit annealing of G-6-Pase specific probes that are labelled. The probes are preferably labelled with radioisotopes or fluorescent reporters.

2. Measurement of G-6-Pase Protein and Antibodies to G-6-Pase

In addition to the detection of G-6-Pase genes or G-6-Pase gene expression using nucleic acid hybridization technology, one can also use immunoassays to detect either the G-6-Pase gene product or the presence of antibodies to G-6-Pase. Since G-6-Pase is expressed only in the liver, kidney and intestine, the determination of G-6-Pase activity or protein should be performed on tissue biopsies from these organs. Immunoassays can be used to qualititatively or quantitatively analyze G-6-Pase protein or G-6-Pase antibodies. A general overview of the applicable technology can be found in Harlow and Lane, Antibodies: A Laboratory Manual, Cold Spring Harbor Pubs., N.Y. (1988), incorporated herein by reference.

a. Antibody Production

A number of immunogens may be used to produce antibodies specifically reactive with G-6-Pase antigen. Recombinant G-6-Pase protein is the preferred immunogen for the production of monoclonal or polyclonal antibodies. Naturally occurring G-6-Pase protein may also be used either in pure or impure form. Synthetic peptides made using the G-6-Pase protein sequences described herein may also used as an immunogen for the production of antibodies to G-6-Pase protein.

Preferentially, recombinant G-6-Pase protein or a fragment thereof is expressed in bacterial cells as described above, and purified as generally described above and in the examples. The product is then injected into an animal capable of producing antibodies. Either monoclonal or polyclonal antibodies may be generated, for subsequent use in immunoassays to measure the G-6-Pase protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the G-6-Pase protein. When appropriately high titers of antibody to the immunogen are obtained, blood is collected from the animal and antisera is prepared. Further fractionation of the antisera to enrich for antibodies reactive to G-6-Pase protein can be done if desired. (See Harlow and Lane, supra.)

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, Eur. J. Immunol. 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

This invention also embraces diagnostic kits for detecting the presence or absence of G-6-Pase in tissue or blood samples which comprises a container holding a nucleotide sequence that is capable of discriminating between wild-type and mutant G-6-pase, a container holding a reagent for detecting the nucleotide sequence that has hybridized to the sample sequence and instructional material for performing the test. This invention further embraces diagnostic kits for detecting the presence of G-6-Pase DNA or RNA in tissue or blood samples which comprise nucleic probes as described herein and instructional material.

H. Gene Therapy Applications

A variety of human diseases may be treated by therapeutic approaches that involve stably introducing a gene into a human cell such that the gene may be transcribed and the gene product may be produced in the cell. Diseases amenable to treatment by this approach include inherited diseases, particularly those diseases such as GSD Type 1a where the defect is with a single gene. For discussions on the application of gene therapy towards the treatment of genetic as well as acquired diseases See Miller, A.D. (1992) Nature 357:455–460, and Mulligan, R.C. (1993) Science 260:926–932, both incorporated herein by reference.

Delivery of the gene or genetic material into the cell is the first critical step in gene therapy treatment of disease. A variety of methods have been used experimentally. Most research has focused on the use of retroviral and adenoviral vectors for gene delivery into the cell. Retroviral vectors have the ability to stably integrate the transferred gene sequences into the chromosomal DNA of the target cell. Retroviral vectors are particularly attractive because they are very efficient in stably transducing a high percentage of target cells. Accordingly most of the approved gene therapy clinical protocols use retroviral vectors. See Miller, A.D., (1992) supra.

Retroviral vectors are particularly useful for modifying cells because of the high efficiency with which the retroviral vectors transduce target cells and integrate into the target cell genome. Additionally, the retroviruses harboring the retoviral vector are capable of infecting cells from a wide variety of tissues.

Retroviral vectors are produced by genetically manipulating retroviruses. Retroviruses are called RNA viruses because the viral genome is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site). See Mulligan, R.C., In: Experimental Manipulation of Gene Expression, M. Inouye (ed), 155–173 (1983); Mann, R., et al., Cell, 33:153–159 (1983); Cone, R.D. and R.C. Mulligan, Proceedings of the National Academy of Sciences, U.S.A., 81:6349–6353 (1984).

The design of retroviral vectors is well known to one of skill in the art. See Singer, M. and Berg, P. supra. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including European Patent Application EPA 0 178 220, U.S. Pat. No. 4,405,712, Gilboa, Biotechniques 4:504–512 (1986), Mann, et al., Cell 33:153–159 (1983), Cone and Mulligan, Proc. Natl. Acad. Sci. USA 81:6349–6353 (1984), Eglitis, M.A, et al. (1988) Biotechniques 6:608–614, Miller, A.D. et al. (1989) Biotechniques 7:981–990, Miller, A.D.(1992) Nature, supra, Mulligan, R.C. (1993), supra. and Gould, B. et al., and International Patent Application No. WO 92/07943 entitled "Retroviral Vectors Useful in Gene Therapy". The teachings of these patents and publications are incorporated herein by reference.

The retroviral vector particles are prepared by recombinantly inserting the gene encoding G-6-Pase into a retrovirus vector and packaging the vector with retroviral capsid proteins by use of a packaging cell line. The resultant retroviral vector particle is incapable of replication in the host cell and is capable of integrating into the host cell genome as a proviral sequence containing the G-6-Pase gene. As a result, the patient is capable of producing G-6-Pase and metabolize glycogen to completion.

Packaging cell lines are used to prepare the retroviral vector particles. A packaging cell line is a genetically constructed mammalian tissue culture cell line that produces the necessary viral structural proteins required for packaging, but which is incapable of producing infectious virions. Retroviral vectors, on the other hand, lack the structural genes but have the nucleic acid sequences necessary for packaging. To prepare a packaging cell line, an infectious clone of a desired retrovirus, in which the packaging site has been deleted, is constructed. Cells comprising this construct will express all structural proteins but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13. See Miller et al., J. Virol. 65:2220–2224 (1991), which is incorporated herein by reference. Examples of other packaging cell lines are described in Cone, R. and Mulligan, R.C., Proceedings of the National Academy of Sciences, USA, 81:6349–6353 (1984) and in Danos, O. and R.C. Mulligan, Proceedings of the National Academy of Sciences, USA, 85: 6460–6464 (1988), Eglitis, M.A., et al. (1988) supra and Miller, A.D., (1990) supra, also all incorporated herein by reference.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

The following examples are offered by way of illustration, not by way of limitation.

EXAMPLES

Example 1: Cloning, Expression and Characterization of Murine G-6-Pase.

a) Library Construction and Screening

To isolate cDNAs encoding G-6-Pase, it was possible to take advantage of an albino deletion mutant mouse which is known to express markedly reduced levels of G-6-Pase activity, as shown by Glueksohn-Waelsch, S. in Cell 15, 225–237 (1979). The primary defect of this mutant mouse is the loss of the fumarylacetoacetate hydrolase gene located around the albino locus on chromosome 7 according to Ruppert, S. et al. in Gene Dev. 6, 1430–1433 (1992). Fumarylacetoacetate hydrolase is the final enzyme in the tyrosine degradation pathway and a deficiency of this enzyme leads to the accumulation of toxic tyrosine metabolites resulting in reduced expression of a group of liver-specific proteins, including G-6-Pase. This reduced expression is documented in more detail by Ruppert, S., et al. in Cell 61, 895–904 (1990). Newborn homozygous deletion mice develop hypoglycemia shortly after birth, correlating with undetectable levels of G-6-Pase activity. This example illustrates how one can isolate a full-length cDNA encoding murine liver microsomal G-6-Pase by screening a normal mouse liver cDNA library differentially with probes representing mRNA populations from the normal and the albino deletion mutant mouse.

A cDNA library in λgt10 representing wild-type homozygote ($C^{ch}/C^{ch}$) mouse liver mRNA, was screened differentially with probes representing the mRNA populations from the wild-type and the albino deletion mutant mouse according to the method described by Ruppert, S., et al. supra. Using this screening method it was possible to isolate the cDNA clone designated pmG-6-Pase-1 which contains nucleotides 12 to 2259 of the murine G-6-Pase.

To obtain the murine G-6-Pase genomic sequence, a mouse liver genomic library was produced in the Lambda Dash system from Stratagene and screened using pmG-6-Pase-1 as the probe.

For sequencing, the cDNA and genomic sequences were each subcloned into pGEM® and sequenced using the GemSeq® transcript sequencing system from Promega Biotech of Madison, Wis. Both strands of the cDNA and genomic clones were sequenced by the Sanger dideoxy chain-termination method described in Proc. Natl. Acad. Sci. USA 74, 5463–5467 (1977). The genomic sequences were compared to cDNA sequences to identify intron-exon junctions.

b) Genomic Sequence Characterization

Nucleotide sequence analysis of the 2248-bp insert of the pmG-6-Pase-1 cDNA (nucleotides 12 to 2259) revealed an open reading frame of 1071 nucleotides that encodes a 357-amino acid polypeptide. The pmG-6-Pase-1 cDNA probe was used to screen a Lambda Dash mouse genomic library and a genomic clone containing the entire murine G-6-Pase transcription unit was isolated and extensively characterized. The genomic organization of the murine G-6-Pase gene was defined by restriction endonuclease mapping, Southern-blot hybridization, and DNA sequencing. The murine gene spans approximately 10 kb and consists of 5 exons: I (311 bp), II (110 bp), III (106 bp), IV (116 bp), and V (1615 bp).

The transcription initiation site of murine G-6-Pase was demonstrated by the following primer extension experiments. Three antisense oligonucleotides corresponding to nucleotides 162 to 181, 127 to 146, and 54–73 of pmG-6-Pase cDNA were labeled at the 5'-OH end with [γ-$^{32}$P] ATP using polynucleotide kinase. Newborn mouse liver poly(A)$^+$ RNA (10 µg) was incubated overnight at 42° C. with 10$^6$ cpm of a primer in hybridization buffer (10 mM Pipes, pH 6.4, 400 mM NaCl and 1 mM EDTA). The samples were extended with AMV reverse transcriptase (20 U, Boehringer Mannheim Biochemicals, IN) for 60 min at 42° C. in 40 µl of a solution containing 50 mM Tris-HCl, pH 8, 100 mM KCl, 10 mM MgCl$_2$, and 0.5 mM each of dNTP. The extended fragments were analyzed on 8% polyacrylamide-urea sequencing gels.

Comparison of the nucleotide and deduced amino acid sequences of pmG-6-Pase cDNA with that in the databases indicated no significant identity to any sequence reported to date. The deduced G-6-Pase protein has a calculated molecular mass of 40 kDa and contains an ER protein retention signal, motifs for protein glycosylation, and several membrane spanning segments. This suggests that this cDNA may encode microsomal G-6-Pase, a glycoprotein of 35 to 36.5 kDa, as reported by Speth, M. and H.-U. Schulze, supra. and Countaway, J.L., et al., J. Biol. Chem. 263:2673 (1988).

c) In vitro Transcription and Translation.

These experiments were done using the TnT coupled reticulocyte lysate system obtained from Promega. The pmG-6-Pase-1 cDNA was analyzed in both sense and anti-sense orientations and the in vitro synthesized proteins were analyzed by 10% polyacrylamide-SDS gel electrophoresis and fluorography. The G-6-Pase, produced by translating the in vitro transcript of pmG-6-Pase-1 cDNA, migrated on SDS-polyacrylamide gel as a 34 kDal polypeptide. The reason this is less than the predicted molecular size of 40 kDal is most likely due to the anomalous electrophoretic mobility caused by the extremely hydrophobic nature of the protein. Applying hydropathy index analysis methods described by Kyte, J., et al., in J. Mol. Biol. 157, 105–132 (1982), and also by Klein, P., et al., Biochim. Biophys. Acta. 815, 468–476 (1985), a total of 6 putative membrane-spanning segments are located in the G-6-Pase protein.

d) Expression in COS-1 cells

To characterize the G-6-Pase encoded by the cDNA, microsomal preparations from transfected COS-1 cells were compared with the hepatic G-6-Pase activities of microsomes isolated from adult mouse liver.

COS-1 cells were grown at 37° C. in HEPES-buffered Dulbecco modified minimal essential medium supplemented with streptomycin, penicillin, and 4% fetal bovine serum. Nucleotides 12 to 1814 of the pmG-6-Pase cDNA (pSV-LmG-6-Pase), which contains the entire coding region at nucleotides 83 to 1153, were subcloned in a pSVL vector (Pharmacia, Piscataway, N.J.) and transfected into COS-1 cells by the DEAE-dextran/chloroquine method describes by Ausubel, F. M., et al., in Current Protocols in Molecular Biology, Greene Publishing and Wiley-Interscience, New York, N.Y. 9.2.1–9.2.6. (1992). Mock transfections of COS-1 cultures with the pSVL vector were used as controls.

e) Murine G-6-Pase Protein Characterization

Microsomal membranes were isolated by the method of Burchell et al. supra. Samples were taken from either Swiss Webster mice which had been fasted overnight or freshly prepared homogenates of pSVLmG-6-Pase-transfected COS-1 cells. Disrupted microsomal membranes were prepared by incubating intact membranes in 0.2% deoxycholate for 20 min at 0° C. The latency or intactness of microsomal preparations was assessed by assaying mannose-6-phosphohydrolysis in intact versus detergent-disrupted microsomes as described by Arion, W. J., et al., J. Biol. Chem. 255, 10396–10406 (1980) incorporated herein by reference.

Phosphohydrolase activity was determined essentially as described by Burchell et al. Supra. Reaction mixtures (100 μl) contained 50 mM cacodylate buffer, pH 6.5, 10 mM glucose-6-P (or mannose-6-P), 2 mM EDTA, and appropriate amounts of microsomal proteins. After incubation at 30° C. for 10 min, reactions were stopped by the addition of 4 volumes of a solution containing 2.1 mM ammonium molybdate, 0.33 M sulfuric acid, 3.3% SDS, and 0.07 M ascorbic acid. Sample absorbance was determined at 820 nm and is related to the amount of phosphate released using a standard curve constructed by a stock of inorganic phosphate solution.

i) Enzyme Reaction Latency

Nordlie, R.C., et al., in The Enzymes of Biological Membranes (eds Martonosi, A. N.) 349–398 (Plenum Press, N.Y., 1985) 2nd Ed. Hepatic describes "latency" for G-6-Pase referring to the portion of enzymatic activity which is not expressed unless the microsomes are disrupted. Microsomal G-6-Pase has varying degrees of latency depending on the substrate utilized. Both glucose-6-P and mannose-6-P are rapidly hydrolyzed in disrupted microsomes, but Arion, W. J., et al., describes in J. Biol. Chem. 247, 2558–2565 (1972) that only glucose-6-P is hydrolyzed in intact microsomes. Therefore, mannose-6-P phosphohydrolysis in intact versus detergent-disrupted microsomes is used to measure the latency or intactness of microsomal preparations. Latencies for mannose-6-P phosphohydrolysis are generally 95% or greater in rat liver microsomes, Nordlie, R.C., et al., supra. However, latencies determined with microsomes derived from isolated rat hepatocytes or hepatoma cells are consistently lower (about 40–54%) than those determined using whole liver, Jorgenson, R. A., et al., J. Biol. Chem. 255, 5907–5915 (1980). In agreement with values reported for microsomal G-6-Pase of the rat, mannose-6-P phosphohydrolase activity in microsomes isolated from mouse livers and pSVLmG-6-Pase-transfected COS-1 cells exhibited latency values of 97% and 50%, respectively (Table 1). Therefore, microsomes of cultured cells have similarly reduced latencies.

ii) Enzyme Thermal Lability

Hepatic G-6-Pase is characterized by its high thermal lability; G-6-Pase is completely inactivated by incubating the microsomal preparation (or homogenate) at pH 5.0 for 10 min at 37° C., Hers, H. G., in Advances in Metabolic Disorders Vol 1 (eds Levine, R., Luft, L.), 1–44 (Academic Press, London, 1964). Under the same conditions, the majority of nonspecific phosphatases, including acid and alkaline phosphatases, are still capable of hydrolyzing glucose-6-P. Incubation of microsomes isolated from pSVLmG-6-Pase-transfected COS-1 cells or adult mouse livers at 37° C. for 10 min at pH 5.0 abolished glucose-6-P phosphohydrolase activity (Table 1), demonstrating that the expressed enzyme and mouse liver microsomal G-6-Pase have similar thermal lability.

iii) Enzyme pH Profile

The pH profiles of glucose-6-P phosphohydrolase activity in disrupted microsomes prepared from pSVLmG-6-Pase-transfected COS-1 cells and adult mouse liver were virtually identical. The pH optimum is close to 6.5 in both preparations, in agreement with the pH profile obtained for rat liver microsomal G-6-Pase, Arion, W. J., et al., J. Biol. Chem. 247, 2558–2565 (1972).

iv) Enzyme Kinetics

Kinetic studies of phosphohydrolysis, with either glucose-6-P or mannose-6-P as the substrate, were performed with microsomes isolated from pSVLmG-6-Pase-transfected COS-1 cells and adult mouse livers. It was previously reported for rat by Arion, W. J., et al., in J. Biol. Chem. 255, 10396–10406 (1980) as well as by Lange, A. J., et al., J. Biol. Chem. 261, 101–107 (1986) that the $K_m$ values of glucose-6-P hydrolysis in intact microsomes are higher than in disrupted microsomes. In this study, we also observed a higher $K_m$ value for glucose-6-P hydrolysis for intact (3.3 mM) versus disrupted (0.68 mM) microsomes of adult mouse livers, demonstrating the similarities between mouse and rat microsomes. We observed little increase in the $K_m$ value for glucose-6-P hydrolysis using intact microsomes from pSVLmG-6-Pase-transfected cells because of the reduced latency (Table 1). Consequently, the kinetic parameters for G-6-Pase in transfected cells were determined for deoxycholate-disrupted microsomal preparations. The $K_m$ values for glucose-6-P and mannose-6-P hydrolysis were indistinguishable between microsomes of pSVLmG-6-Pase-transfected COS-1 cells and adult mouse livers (Table 1). Moreover, these values were similar to those reported for rat microsomal glucose-6-P and mannose-6-P phosphohydrolysis. Additionally, the $V_{max}$ values for both microsomal preparations are virtually identical (Table 1) and are in agreement with those reported previously for rat liver microsomes.

v) Enzyme Inhibitor Assays

Vanadate is a potent inhibitor of glucose-6-P phosphohydrolase activity as reported by Singh, J., et al., Biochem. Acta 678, 477–482 (1981). Microsomal preparations from both pSVLmG-6-Pase-transfected COS-1 cells and adult mouse livers were equally sensitive to vanadate, giving nearly identical inhibition curves of glucose-6-P hydrolysis. Moreover, vanadate was a competitive inhibitor of glucose-6-P phosphohydrolysis in both microsomal preparations, yielding essentially identical $K_i$ values (Table 1). The $K_i$ values (0.33–0.34 mM) for vanadate observed in the present study differed considerably from the $K_i$ for vanadate (1.5 μM) reported for permeable hepatocytes or rat microsomes. The reason for this discrepancy is unknown. However, a similar vanadate inhibition curve to that for the mouse G-6-Pase reported here was observed for commercially obtained crude microsomal preparations of rabbit G-6-Pase obtained from Sigma Chemical Co., St. Louis.

In addition to displaying phosphohydrolytic activity, G-6-Pase is capable of catalyzing the formation of glucose-6-P from glucose and a variety of phosphate substrate donors, Nordlie, R.C. and Sukalski, K.A., supra. G-6-Pase is thought to play a role in controlling the flow of glucose between the hepatocyte and blood by tightly regulating the equilibrium between glucose phosphorylation and the hydrolysis of glucose-6-P.

Phosphotransferase activity was determined by a modification of the method described by Jorgenson and Nordlie, supra. Reaction mixture (10 µl) contained 100 mM HEPES buffer, pH 6.5, 50 mM glucose, [U–$^{14}$] D-glucose ($10^5$ cpm/reaction, 256 mCi/mmol, ICN Biochemicals, Irvine, Calif.), 4 mM carbamyl-P, and deoxycholate-disrupted microsomal proteins. After incubation at 30° C. for 10 min, reactions were stopped by heating at 80° C. for 5 min. The samples were then centrifuged at 10,000×g for 5 min, and 2 to 4 µl of supernatant applied to a PEI-cellulose plate (J. T. Baker, Inc., Phillipsburg, N.J.). Glucose-6-P was separated from glucose by thin-layer chromatography developed in water. Spots were quantitated on an AMBIS Radioanalytic Imaging System (San Diego, Calif.).

Table 1 shows phosphohydrolase and phosphotransferase activities in microsomes of pSVLmG-6-Pase-transfected COS-1 cells and adult mouse livers were evaluated. Similar specific transferase activities were observed in both microsomal preparations, in good agreement with the value (0.294 µmole/min/mg of microsomal protein) reported for carbamyl-P: glucose phosphotransferase activity in rat hepatocyte microsomes.

TABLE 1

Characteristics of microsomal G-6-Pase activity in pSVLmG-6-Pase-transfected COS-1 cells and adult mouse livers.

| Parameters | pSVLmG-6-Pase-Transfected COS | Mouse Liver |
|---|---|---|
| Phosphohydrolase[c] | | |
| Latency | 50% | 97% |
| Thermal Stability[b] | 1.6% | <1% |
| Glucose-6-P, $K_m$ | 0.65 ± 0.09 | 0.68 ± 0.03 |
| Mannose-6-P, $K_m$[a] | 0.67 ± 0.07 | 0.67 ± 0.04 |
| Glucose-6-P, $V_{max}$ | 0.21 ± 0.05 | 0.35 ± 0.06 |
| Mannose-6-P, $V_{max}$ | 0.20 ± 0.06 | 0.30 ± 0.08 |
| Vanadate, $K_i$ | 0.34 | 0.33 |
| Phosphotransferase[d] | | |
| Carbamyl-P: Glucose | 0.22 | 0.3 |

[a]Latency for mannose-6-P (5 mM) hydrolysis, defined as (1-intact/disrupted) × 100, was performed in microsomes prepared from two independent batches of pSVLm-G-6-Pase-transfected COS-1 cells and three different adult mouse livers. Activities were the average of three determinations.
[b]Thermal stability was determined by assaying glucose-6-P phosphohydrolase activity in deoxycholate (0.2%) disrupted microsomal membranes, before and after incubation at 37° C. for 10 min at pH 5.0, and refers to enzyme activities remaining after heat treatment.
[c]In the phosphohydrolase assay, the $K_m$ and $K_i$ values are expressed in mM; $V_{max}$ as µmol/min/mg of microsomal protein. $K_m$ and $K_i$ values represent the mean ± SEM.
[d]The values for phosphotransferase activities (µmol/min/mg of microsomal protein) were obtained from the linear region of enzyme concentration curves. Mock transfected COS-1 cells exhibited <1% of the total thermal sensitive phosphohydrolytic or phosphotransferase activities.

Example 2: Cloning, Expression and Characterization of Human G-6-Pase.

a) Library Construction and Screening

Using a pair of oligonucleotide primers derived from the murine G-6-Pase cDNA, we isolated a human G-6-Pase cDNA clone, phG-6-Pase-1 by reverse transcriptase-polymerase chain reaction (RT-PCR) using human liver poly(A)$^+$ RNA. Human liver cDNAs were synthesized by incubating human liver poly(A)$^+$ RNA (5 µg) for 1 h at 42° C. in a reaction mixture (20 µl) containing 10 mM Tris HCl, pH 8.3, 50 mM KCl, 5 mM MgCl$_2$,1 mM dNTPs, 1.6 µg oligo-p(dT)$_{15}$ primer, 50 units of RNasin, and 20 units of AMV reverse transcriptase. The phG-6-Pase-1 cDNA clone was isolated by PCR amplification of human liver cDNAs using two oligonucleotide primers deriving from nucleotides 76 to 96 (5'-AAGGATGGAGGAAGGAATGAA-3', sense (Seq. ID No.:7)) and 1156 to 1136 (5'-GCCTTACAAAGACTTCTTGTG-3', antisense (Seq. ID No.:8)) of the murine G-6-Pase cDNA. The sense and antisense primers contain additional XhoI and XbaI linkers, respectively, and after digestion with XhoI and XbaI, the amplified fragment was subcloned into a pGEM vector (Promega) or a pSVL (Pharmacia) vector. The identity of the phG-6-Pase-1 clone was confirmed by DNA sequencing.

b) Genomic Sequence Characterization

The human G-6-Pase gene was isolated from a human leukocyte genomic library in λAEMBL-3 (Clontech) using the phG-6-Pase-1 cDNA probe. The human G-6-Pase gene spans approximately 12.5 kb and consists of 5 exons: I (309 bp), II (110 bp), III (106 bp), IV (116 bp) and V (larger than 2,000 bp including a coding region of 509 bp).

The 5'- and 3'-untranslated regions of the human G-6-Pase mRNA were identified by a combination of primer extension, sequencing of the human G-6-Pase genomic clone, and RT-PCR. The transcription initiation site of the G-6-Pase mRNA was determined by primer extension using human liver poly(A)$^+$ RNA as a template and an antisense oligonucleotide primer corresponding to nucleotides 124 to 142 of the human G-6-Pase cDNA. To demonstrate that the 3'-untranslated region of the G-6-Pase cDNA (nucleotides 1154 to 2806) was contained in the region 3' of the termination codon in exon 5 of the human G-6-Pase gene, we utilized four pairs of oligonucleotide primers to amplify individually the 3'-untranslated region of the G-6-Pase mRNA by RT-PCR using human liver poly(A)$^+$ RNA as a template. The 4 pairs of primers are: 3UT1 (nucleotides 1155 to 1172, Sense) and 3UT2 (nucleotides 1934 to 1950, antisense), 3UT3 (nucleotides 1886 to 1902, sense) and 3UT4 (nucleotides 2242 to 2258, antisense), 3UT3 and 3UT5 (nucleotides 2490 to 2506, antisense), 3UT3 and 3UT6 (2783 to 2800, antisense) Four predicted fragments of 796, 373, 621, and 915 bp were obtained, subcloned, and their identities confirmed by DNA sequencing. A consensus motif for polyadenylation (AATAAA) is located at nucleotides 3053–3058.

The endoplasmic reticulum (ER) localization of the human G-6-Pase is predicted by the presence of an ER protein retention signal KK, M. R. Jackson, et al., EMBO J. 9, 3153 (1990), positioned 3 and 4 amino acids from the carboxyl terminus, respectively. The hydropathy index analysis shows human G-6-Pase to be similiar to murine G-6-Pase in that the protein is an extremely hydrophobic protein containing 6 putative membrane-spanning segments.

c) Protein Characterization

The functional identity of the human G-6-Pase cDNA was studied in a manner similiar to that described above with the murine G-6-Pase. Detailed biochemical studies were performed on microsomal preparations isolated from COS-1 cells transiently transfected with the phG-6-Pase-1 cDNA and compared with activities in human liver microsomes.

Latency values for mannose-6-P phosphohydrolase activity reported for human liver microsomes varied from 23–26% (Lange, A.J. and W.J. Arion, J. Biol. Chem. 255:2558, (1983), Nordlie, R. C., et al., J. Biol. Chem. 258:9739–9744, (1983)) to 95% (Burchell, A., et al., supra)). Human liver microsomes isolated in the present study exhibited a latency value of 75% (Table 2). Microsomes isolated from rat hepatocytes or hepatoma cells have been shown to exhibit reduced latencies (Jorgenson, R.C. and R.C. Nordlie, J. Biol. Chem., 255:5907 (1980), comparable to that from phG-6-Pase-1-transfected COS-1 cells which displayed a latency of 28% (Table 2). Cultured cells thus, exhibit similarly reduced latencies.

Hepatic G-6-Pase is known to be completely inactivated by incubating the microsomal preparation at pH 5.0 for 10 min at 37° C. (Hers, H.G., in Advances in Metabolic Disorders, R. Levine, L. Luft, Eds. (Academic Press, London, 1964) Vol 1, pp. 1–44). Incubation of microsomes isolated from phG-6-Pase-1-transfected COS-1 cells or human livers at 37° C. for 10 min at pH 5.0 virtually abolished glucose-6-P phosphohydrolase activity (Table 2), demonstrating that the expressed enzyme is indistinguishable from the human liver microsomal G-6-Pase. Kinetic studies (Table 2) indicated that $K_m$ values for glucose-6-P and $K_i$ values for a competitive inhibitor, vanadate (Singh, J., et al., Biochim. Biophys. Acta., 678:477 (1981), were indistinguishable between microsomes isolated from phG-6-Pase-1-transfected COS-1 cells and human livers. Taken together, our data demonstrate that this cDNA encodes human microsomal G-6-Pase, the enzyme deficient in GSD type 1a patients.

TABLE 2

Characteristics of microsomal G-6-Pase phosphohydrolase activity in phG-6-Pase-1-transfected COS-1 cells and human liver.

| | Latency[a] | Thermal[b] Stability | Glucose-6-P $K_m$ (mM) | Vanadate $K_i$ (mM) |
|---|---|---|---|---|
| phG-6-Pase-1-COS | 28.2% | 6.0% | 1.77 ± 0.13 | 1.68 |
| Human Liver | 75.4% | 4.1% | 1.71 ± 0.11 | 1.61 |

[a]Latencies were assessed by mannose-6-P phosphohydrolysis in intact (I) versus detergent-disrupted (D) microsomes, defined as (1-I/D) × 100. Two microsomal preparations from phG-6-Pase-1-transfected COS-1 cells or human livers were analyzed.
[b]Thermal stability was determined by assaying glucose-6-P phosphohydrolase activity in deoxycholate (0.2%) disrupted microsomes before and after incubation for 10 min at 37° C. in 50 mM cacodylate buffer, pH 5.0 and refers to enzyme activities remaining after heat treatment.

Example 3: Identification of Human G-6-Pase Mutations.

a) Sequence Amplification

To identify the G-6-Pase gene mutations in GSD type 1a patients, we PCR amplified the coding regions of each of the 5 exons and all intron-exon junction regions of this gene using five pairs of oligonucleotide primers containing intronic sequences. Five pair of oligonucleotide primers containing intronic sequences of the G-6-Pase gene were used to amplify by PCR the coding regions of each of the 5 exons and the corresponding intron-exon junctions in the G-6-Pase genes of GSD type 1a patients and available family members.

i) Exon I primer pair design:
Primer 1s is contained in the following nucleotides 1 to 82 in exon I: 5'-TAGCAGAGCAATCACCACCAAGCCTG-GAATAACTGCAAGGGC TCTGCTGACATCTTCCTGAGGTGCCAAGGAAATGA-GGATG-3' (Seq. ID No.:9) (ATG is the protein initiation codon) Primer 1as is contained in the following nucleotide sequence from intron 1 at the junction of Exon I/Intron 1: 5'-GTAAGAACCATATAGAGAGGAGAT CAGCAAGAAAAGAGGCTGGCATT-3' (Seq. ID No.:10). Primer 1s: 5'-TCTGCTGACATCTTCCT-3' (Seq. ID No.:11). Primer 1as: 5'-GCCTCTTTTCTTGCTG-3' (Seq. ID No.:12).

ii) Exon II primer pair design:
Primer 2s is contained in intron 1 at the junction of Intron 1/Exon II: 5'-AAAA GCATTCATTCAGTAACCCCAGAAACTTGTTCTGTTT-TTCCATAG-3' (Seq. ID No.:13). Primer 2as is contained in intron 2 at the junction of Exon II/Intron 2: 5'-GTAAGCGTCCCAGCCCCTG CAGACAGAAGCTGAGTGGACCTCGTTT-3' (Seq. ID No.:14). Primer 2s: 5'-GCATTCATTCAGTAACCC-3' (Seq. ID No.:15). Primer 2as: 5'-TCCACTCAGCTTCTGTCTG-3' (Seq. ID No.:16).

iii) Exon III primer pair design:
Primer 3s is contained in intron 2 at the junction of intron 2/Exon III: 5'-CTTTT CACCTTTACTCCATTCTCTTTCCTGCCCTTTAG-3' (Seq. ID No.:17). Primer 3as is contained in intron 3 at the junction of Exon III/Intron 3: 5'-GTAAGAACTCAC-CACTGGGGTGTAGGTGGTGGA- GGGCAGGAGGC AGCTCTCTC TGTAGCTGACACACCACGTATCTTCC-3' (Seq. ID No.:18). Primer 3s: 5'-CACCTTTACTCCATTCTC-3' (Seq. ID No.:19). Primer 3as: 5'-GTGGTGTGTCAGCTACA-3' (Seq. ID No.:20).

iv) Exon IV primer pair design:
Primer 4s is contained in intron 3 at the junction of Intron 3/Exon IV: 5'-AGTTT GCCAGGCTCCAACATTTCTGCAGGGGCTGTTTTCTT-TGCTGAAGGATCT GCACCTGTGTTCTGTTATGGT-TGCCTCTTCTGTTGCAG-3' (Seq. ID No.:21). Primer 4as is contained in intron 4 at the function of Exon IV/Intron 4 5'-GTATGGGCTGATCTGACTCCCTTCCT-TCTCCCCCAAACCCCATTCCGTTTCTCTCC CTAAT-CAGGA-3' (Seq. ID No.:22). Primer 4s: 5'-GCCAGGCTC-CAACATTT-3' (Seq. ID No.:23). Primer 4as: 5'-GGAGAGAAACGGAATGG-3' (Seq. ID No.:24).

v) Exon V primer pair design:
Primer 5s is contained in intron 4 at the junction of Intron 4/Exon V: 5'-GTCCCAAATC CTTCCTATCTCTCACAGTCATGCTTTCTTCCACTCA-G-3' (Seq. ID No.:25). Primer 5as is contained in the noncoding region in Exon V: 5'-TAAGAGATGTG-GAGTCTTCGGTGTTTAAAGTCA- ACAACCATGC-CAGGGA TTGAGGAGGACTACTATTTGAAG-CAATGGGCACTGGTATTTGGAGCAAGTGA-3' (Seq. ID No.:26). (TAA is the protein chain termination codon) Primer 5s: 5'-CTTCCTATCTCTCACAG-3' (Seq. ID No.:27). Primer 5as: 5'-TCACTTGCTCCAAATACC-3' (Seq. ID No.:28). The amplified fragments, I (306), II (191), III (209) IV (259), and V (646), were subcloned and five subclones of each exon were sequenced and compared with that of a normal G-6-Pase gene.

b) Patient LP, Homozygote Having TA Insertion at Nucleotide 459

The analysis of the G-6-Pase gene in the GSD type 1a patient LP showed that exons I, II, IV, and V were normal. However, exon 3 of the G-6-Pase gene had a TA insertion at nucleotide 459 which was identified in each of the five exon III subclones examined. The 2-basepair insertion alters the reading frame of the encoded protein such that a stop codon is generated at nucleotides 467 to 469. The predicted mutant G-6-Pase is a severely truncated protein of 129 amino acids. These results indicate that LP is homozygous for the TA insertion and predict that the mother (only parent available) is heterozygous for the insertion at this locus. As expected, a TA insertion at nucleotide 459 was demonstrated in two of five exon III subclones of the gene from the mother of LP.

c) Patient LLP: Compound Heterozygote with Mutation of Arg[83] to Cys and Gln[347] to Stop Codon Analysis of the G-6-Pase gene in a GSD type 1a patient, LLP, showed that exons I, III, and IV were normal. In exon II of LLP, a C to T mutation at nucleotides 326 converts an arginine codon to a cysteine (codon 83) was found in three of the five subclones. A second mutation was observed in two of the five independent exon V subclones of patient LLP. This mutation changed a C to T at nucleotide 1118 which converts a glutamine at codon 347 to a stop codon. G-6-Pase consists of 357 residues, but the predicted mutant G-6-Pase is a truncated protein of 346 amino acids, lacking the ER protein retention signal KK at amino acid 354 and 355. Our results suggest that patient LLP is a compound heterozygote with different mutations in the two G-6-Pase alleles. This was confirmed by sequencing exon subclones obtained from the G-6-Pase gene of both parents. The father had a normal exon II and the mother, a normal exon V. Two of the five exon V subclones from the gene of the father contained a C to T mutation at nucleotide 1118 converting a glutamine to a stop at codon 347. Two of the five exon II subclones from the gene of the mother contained a C to T mutation at nucleotide 326 converting an arginine to a cysteine at codon 83.

d) Patients KB and CB: Homozygotes with Mutation of $Gln^{347}$ to a Stop Codon

In a second patient (KB), exons I, II, III, and IV were normal. However, exon V of the G-6-Pase gene had a C to T mutation nucleotide 1118 which converts a glutamine at codon 347 to a stop codon. This mutation was identified in each of the five exon V subclones examined, indicating that KB is homozygous for this mutation and predicting that both parent is heterozygous for the C to T substitution at nucleotide 1118 in this locus. As expected, a C to T mutation at nucleotide 1118 was demonstrated in two of six exon V subclones of the gene from the mother and three of the five exon V subclones of the gene from the father of KB. In addition to KB, a second sibling, CB, was also diagnosed to be GSD type 1a. Analysis of the G-6-Pase gene in patient CB indicated that all five exon V clones contained the C to T mutation at nucleotide 1118. Like KB, CB is homozygous for this mutation at both G-6-Pase alleles and the predicted G-6-Pase of CB is a truncated protein of 346 amino acids.

e) Patients PP and AN: Homoygote with Mutation of $Arg^{83}$ to Cys

In patients PP and AN all five subclones of the gene were found to be mutated from a C to a T at nucleotide 326 of exon II, thus converting an arginine codon encoding amino acid 83 to a cysteine codon.

f) Patient PC: Compound Heterozygote with Mutation of $Arg^{83}$ to Cys and $Arg^{295}$ to Cys In patient PC, exons I, III, and IV were normal, however exons II and V each contained a C to T mutation at nucleotides 326 and 962, respectively. Interestingly, both mutations were found to convert an arginine codon to a cysteine codon (codon 83 in exon II and codon 295 in exon V). Our finding, that only two of the five subclones from either exon II or V exhibit the mutation, suggests that patient PC is a compound heterozygote with different mutations in the two G-6-Pase alleles. This was confirmed by sequencing exon subclones obtained from the G-6-Pase gene of both parents. The father had a normal exon II and the mother, a normal exon V. Two of the five exon V subclones from the gene of the father contained a C to T mutation at nucleotide 962 converting an arginine to a cysteine at codon 295. Three of the five exon II subclones from the gene of the mother contained a C to T mutation at nucleotide 326 converting an arginine to a cysteine at codon 83.

The liver biopsy of patient PC had no detectable G-6-Pase activity, suggesting that a mutation which substitutes either $arginine^{83}$ or $arginine^{295}$ to a cysteine residue yields a mutant G-6-Pase with undetectable phosphohydrolase activity. To confirm our conclusions, three G-6-Pase mutants were constructed that changed either $arginine^{83}$ to $cysteine^{83}$ (G-6-Pase-$Cys^{83}$), $arginine^{295}$ to $cysteine^{295}$ (G-6-Pase-$Cys^{295}$), or both arginine residues (G-6-Pase-$Cys^{83}$/$Cys^{295}$).

To construct the above mutants, site-directed mutagenesis was done on a clone containing the entire coding region of the human G-6-Pase cDNA (phG-6-Pase) by the method of Higuchi, R. in PCR Protocols: A Guide to Methods and Applications, Innis, M.A., et al., Eds., Acad. Press, Inc., San Diego, Calif. pp. 177–183 (1990). The two outside PCR primers were 01 (5'-AGGATGGAGGAAGGAATGAA-3' (Seq. ID No.:29), nucleotides 77 to 96) and 02 (5'-TTA-CAACGACTTCTTGTGCGGCTG-3' (Seq. ID No.:30), nucleotides 1153 to 1130). The two pairs of inside mutant primers for G-6-Pase-$Cys^{83}$ mutant are M1S (5'-TGGA-CAGtGTCCATACTGGTGG-3' (Seq. ID No.:31), nucleotides 319 to 340) and M1AS (5'-CCACCAGTATGGA-CaCTGTCCA-3' (Seq. ID No.:32), nucleotides 340 TO 319), and for G-6-Pase-$Cys^{295}$ mutant are M2S (5'-GCTC-CCATTCtGCCTCAGCTC-3' (Seq. ID No.:33), nucleotides 952 to 972) and M2AS (5,-GAGCTGAGGCaGAATGG-GAGC-3' (Seq. ID No.:34), nucleotides 972 to 952). The mutant bases are indicated by lower case letters. 01 and 02 contain an additional XhoI or XbaI linker, respectively. The double mutant G-6-Pase-$Cys^{83}$/$Cys^{295}$ was constructed using G-6-Pase-$Cys^{83}$ as a template and primers, M2S and M2AS. The amplified fragments were digested with XhoI and XbaI and ligated into a pSVL vector. All constructs were confirmed by DNA sequencing.

As predicted, arginine to cysteine substitution at either codon 83 or 295 abolished G-6-Pase phosphohydrolase activity. Northern hybridization analysis of G-6-Pase transcripts from transfected cells showed that wild-type and mutant G-6-Pase mRNAs were expressed at similar levels. Moreover, translation of mutant G-6-Pase mRNA indicated that G-6-pase-$Cys^{83}$, G-6-Pase-$Cys^{295}$, or G-6-Pase-$Cys^{83}$/$Cys^{295}$ RNA supported the synthesis of polypeptides of 34.5 and 37.5 kDa.

There are three potential asparagine-linked glycosylation sites in the deduced protein, predicting that G-6-Pase is glycosylated. SDS-polyacrylamide gel electrophoresis of the protein expressed in the presence of canine microsomal membranes showed that G-6-Pase-wild-type mRNA supported the synthesis of two polypeptides of 31 and 34.5 kDa which were processed to glycosylated polypeptides of 34.5 and 39 kDa respectively. This is in agreement with what Waddell, I.D. and A. Burchell, in Biochem. J. 275, 133 (1991), and Countaway, J. L., et al., in J. Biol. Chem. 263, 2673 (1988), showed for rat microsomal G-6-Pase which migrates as two tightly associated glycopolypeptides of 36.5 kDa,.

All three mutant proteins, G-6-Pase-$Cys^{83}$ G-6-Pase-$Cys^{295}$, and G-6-Pase-$Cys^{83}$/$Cys^{295}$, exhibited a higher apparent molecular weight and markedly reduced processing of the G-6Pase polypeptides. Such shift in apparent molecular weights and protein processing by a single amino acid substitution represents an interesting and unexpected finding. Our data suggest that in human G-6-Pase, mutation of arginine at either codon 83 or 295 to a cysteine induces conformational changes which inactivate the enzyme.

What is claimed is:

1. An isolated nucleic acid selectively hybridizing to nucleic acid encoding a catalytic moiety of the human glucose-6-phosphatase system (G-6-Pase, E.C. 3.1.3.9.), said nucleic acid selectively hybridizing to the sense or antisense strand of the nucleic acid of Seq I.D. No. 1, or to a mutated nucleic acid sequence of Seq I.D. No. 1 wherein said mutation is selected from the group consisting of:

a mutation at nucleotide 459 of Seq I.D. No. 1, said mutation being the insertion of a TA;

a mutation at nucleotide 326 of Seq I.D. No. 1 wherein C is replaced with T;

a mutation at nucleotide 962 of Seq I.D. No. 1 wherein C is replaced with T; and, a mutation at nucleotide 1118 of Seq I.D. No. 1 wherein C is replaced with T; where said hybridization occurs in the presence of a human nucleic acid library said nucleic acid remaining hybridized under hybridization wash conditions consisting of 0.2 X SSC, 0.1% SDS, and 65° C. and the nucleic acid comprises a sequence which hybridizes to a region of the glucose-6-phosphatase catalytic moiety encoding nucleic acid containing at least one of the mutations.

2. The nucleic acid of claim 1 wherein said nucleic acid has a nucleotide sequence encoding Seq I.D. No. 2.

3. The nucleic acid of claim 1 having a nucleotide sequence a mutation at nucleotide with 459, said mutation being the insertion of a TA, said nucleotide sequence encoding Seq I.D. No. 3.

4. The nucleic acid of claim 1 having a nucleotide sequence with a mutation at nucleotide 326 of Seq I.D. No. 1 wherein C is replaced with T, said nucleotide sequence encoding Seq I.D. No. 4.

5. The nucleic acid of claim 1 having a nucleotide sequence with a mutation at nucleotide 962 of Seq I.D. No. 1 wherein C is replaced with T, said nucleotide sequence encoding Seq I.D. No. 5.

6. The nucleic acid of claim 1 having a nucleotide sequence with a mutation at nucleotide 1118 of Seq I.D. No. 1 wherein C is replaced with T, said nucleotide sequence encoding Seq I.D. No. 6.

7. A recombinant vector able to replicate in a prokaryotic or eukaryotic organism, said vector containing a nucleotide sequence encoding a peptide sequence of a catalytic moiety of the human glucose-6-phosphatase system or a mutated catalytic moiety of the human glucose-6-phosphatase system, said peptide sequence selected from the group consisting of: Seq I.D. No. 2, Seq I.D. No. 3, Seq I.D. No. 4, Seq I.D. No. 5, and, Seq I.D. No. 6.

8. The vector of claim 7 being able to replicate in a prokaryotic organism.

9. The vector of claim 7 being able to replicate in a eukaryotic organism.

10. The vector of claim 7 wherein said sequence is operably linked to a promoter.

11. The vector of claim 10 being capable of expressing said amino acid sequence in a prokaryotic host.

12. The vector of claim 10 being capable of expressing said amino acid sequence in an eukaryotic host.

13. A kit for detecting in a test sample the presence or absence of a mutation in a nucleotide sequence encoding a catalytic moiety of the human glucose-6-phosphatase system comprising;

a) a container holding a oligonucleotide whereby said oligonucleotide is capable of discriminating between the wild type glucose-6-phosphatase catalytic moiety gene and a mutant form of the human glucose-6-phosphatase catalytic moiety gene wherein said mutation is selected from the group consisting of:

a mutation at nucleotide 459 of Seq I.D. No. 1, said mutation being the insertion of a TA;

a mutation at nucleotide 326 of Seq I.D. No. 1 wherein C is replaced with T;

a mutation at nucleotide 962 of Seq I.D. No. 1 wherein C is replaced with T; and, a mutation at nucleotide 1118 of Seq I.D. No. 1 wherein C is replaced with T; and the oligonucleotide comprises a sequence which hybridizes to a region of the glucose-6-phosphatase catalytic moiety gene containing at least one of said mutations; and b) a container holding a reagent for detecting the formation of a duplex between the gene and the oligonucleotide sequence.

14. The kit of claim 13 further comprising a PCR primer pair which amplify a region of the nucleotide sequence encoding a catalytic moiety of the human glucose-6-phosphatase system.

15. The kit of claim 13 wherein said mutation is at nucleotide 459 of Seq I.D. No. 1, said mutation is the insertion of a TA.

16. The kit of claim 13 wherein said mutation is at nucleotide 326 of Seq I.D. No. 1 wherein C is replaced with T.

17. The kit of claim 13 wherein said mutation is at nucleotide 962 of Seq I.D. No. 1 wherein C is replaced with T.

18. The kit of claim 13 wherein said mutation is at nucleotide 3918 of Seq I.D. No. 1 wherein C is replaced with T.

19. The kit of claim 13 further comprising an amplification primer pair specifically binding to a human genomic DNA sequence encoding the catalytic moiety of the glucose-6-phosphatase system.

* * * * *